(12) United States Patent
Mershin et al.

(10) Patent No.: US 9,377,447 B2
(45) Date of Patent: *Jun. 28, 2016

(54) METHODS AND APPARATUS FOR ARTIFICIAL OLFACTION

(71) Applicant: Massachusetts Institute of Technology, Cambridge, MA (US)

(72) Inventors: Andreas Mershin, Cambridge, MA (US); Asmamaw Wassie, Cambridge, MA (US); Yael Maguire, Boston, MA (US); David Kong, Lexington, MA (US); Shuguang Zhang, Cambridge, MA (US); Patrick Moran, Shrewsbury, MA (US); Karolina Corin, Johannesburg (ZA)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/815,574

(22) Filed: Jul. 31, 2015

(65) Prior Publication Data

US 2015/0362469 A1    Dec. 17, 2015

Related U.S. Application Data

(63) Continuation of application No. 13/966,169, filed on Aug. 13, 2013, now Pat. No. 9,140,677.

(60) Provisional application No. 61/682,587, filed on Aug. 13, 2012.

(51) Int. Cl.
*G01N 33/00*    (2006.01)
*G01N 27/00*    (2006.01)

(52) U.S. Cl.
CPC ............ *G01N 33/0031* (2013.01); *G01N 27/00* (2013.01)

(58) Field of Classification Search
CPC .......... G01N 33/0004; G01N 33/0022; G01N 33/0031; G01N 27/00; Y10T 436/25875
USPC ............... 436/149, 150, 151, 181; 422/82.01, 422/68.1, 83, 88, 98; 73/23.34
See application file for complete search history.

(56) References Cited

U.S. PATENT DOCUMENTS

| | | | |
|---|---|---|---|
| 6,411,905 B1 | 6/2002 | Guoliang et al. | |
| 6,844,197 B1 | 1/2005 | Doleman et al. | |
| 9,140,677 B2 * | 9/2015 | Mershin | G01N 33/0031 |

OTHER PUBLICATIONS

Chang, J., et al., 2008, Electronic Noses Sniff Success. IEEE Spectrum, Feb. 29, 2008.

(Continued)

*Primary Examiner* — Maureen Wallenhorst
(74) *Attorney, Agent, or Firm* — Stephen R. Otis

(57) ABSTRACT

In exemplary implementations of this invention, an electronic olfactor determines whether a scent being tested matches the scent of a positive control. The electronic olfactor can perform this scent matching even in a changing olfactory environment, and even if the positive control scent is a combination of hundreds or thousands of different odorants. No prior training is needed, and no attempt is made to identify a single odorant that is unambiguously responsible for a scent. Instead, a computer compares the total scent pattern of a positive control sample with the total scent pattern of a test sample, across a sweep of many permutations of electrical inputs to scent sensors, to try to find any condition under which the total scent patterns do not match. If such a condition cannot be found, then the computer declares a match between the test and target scents.

10 Claims, 14 Drawing Sheets

(56) References Cited

OTHER PUBLICATIONS

Di Francesco, F., et al., 2001., An electronic nose for odour annoyance assessment. Atmospheric Environment, vol. 35, Issue 7, 2001, pp. 1225-1234.

Franco, M., et al., 2011, Molecular vibration-sensing component in *Drosophila melanogaster* olfaction. Proceedings of the National Academy of Sciences of the United States of America, Feb. 14, 2011, doi: 10.1073/pnas.1012293108, PNAS Feb. 14, 2011.

Gao, T., et al., 2005, Detection and Classification of Volatile Organic Amines and Carboxylic Acids Using Arrays of Carbon Black-Dendrimer Composite Vapor Detectors. Chem. Mater., 2005, vol. 17, No. 11, pp. 2904-2911, American Chemical Society, 2005.

Goldsmith, B., et al., 2011, Biomimetic Chemical Sensors Using Nanoelectronic Readout of Olfactory Receptor Proteins. ACS Nano, 2011, vol. 5, issue 7, pp. 5408-5416, Web publication date Jun. 22, 2011, American Chemical Society.

Kim, T., et al., 2009, Single-Carbon-Atomic-Resolution Detection of Odorant Molecules using a Human Olfactory Receptor-based Bioelectronic Nose. Advanced Materials, vol. 21, Issue 1, pp. 91-94, Jan. 5, 2009, Article first published online Oct. 30, 2008.

Author Unknown, Electronic Nose. Webpage, Lewis Research Group, Division of Chemistry and Chemical Engineering, California Institute of Techology. Exact date of webpage unknown (May 21, 2011 or earlier), accessed on Dec. 2, 2013 at http://web.archive.org/web/20100521041215/http://nsl.caltech.edu/research:nose.

Nagle, T. et al, 1999, The how and why of electronic noses. IEEE Spectrum, vol. 35 , Issue 9, pp. 22-31, Sep. 1998.

Staples, E., 1999, Electronic nose simulation of olfactory response containing 500 orthogonal sensors in 10 seconds. Proceedings of 1999 IEEE Ultrasonics Symposium, vol. 1, pp. 417-423.

Weiss, T., et al., 2012, Perceptual convergence of multi-component mixtures in olfaction implies an olfactory white. Proceedings of the National Academy of Sciences of the United States of America, published online Nov. 19, 2012, doi: 10.1073/pnas.1208110109, PNAS Nov. 19, 2012.

Yoon, H., et al., I2009, Polypyrrole Nanotubes Conjugated with Human Olfactory Receptors: High-Performance Transducers for FET-Type Bioelectronic Noses. Angewandte Chemie International Edition, vol. 48, issue 15, pp. 2755-2758, published online Mar. 9, 2009.

\* cited by examiner

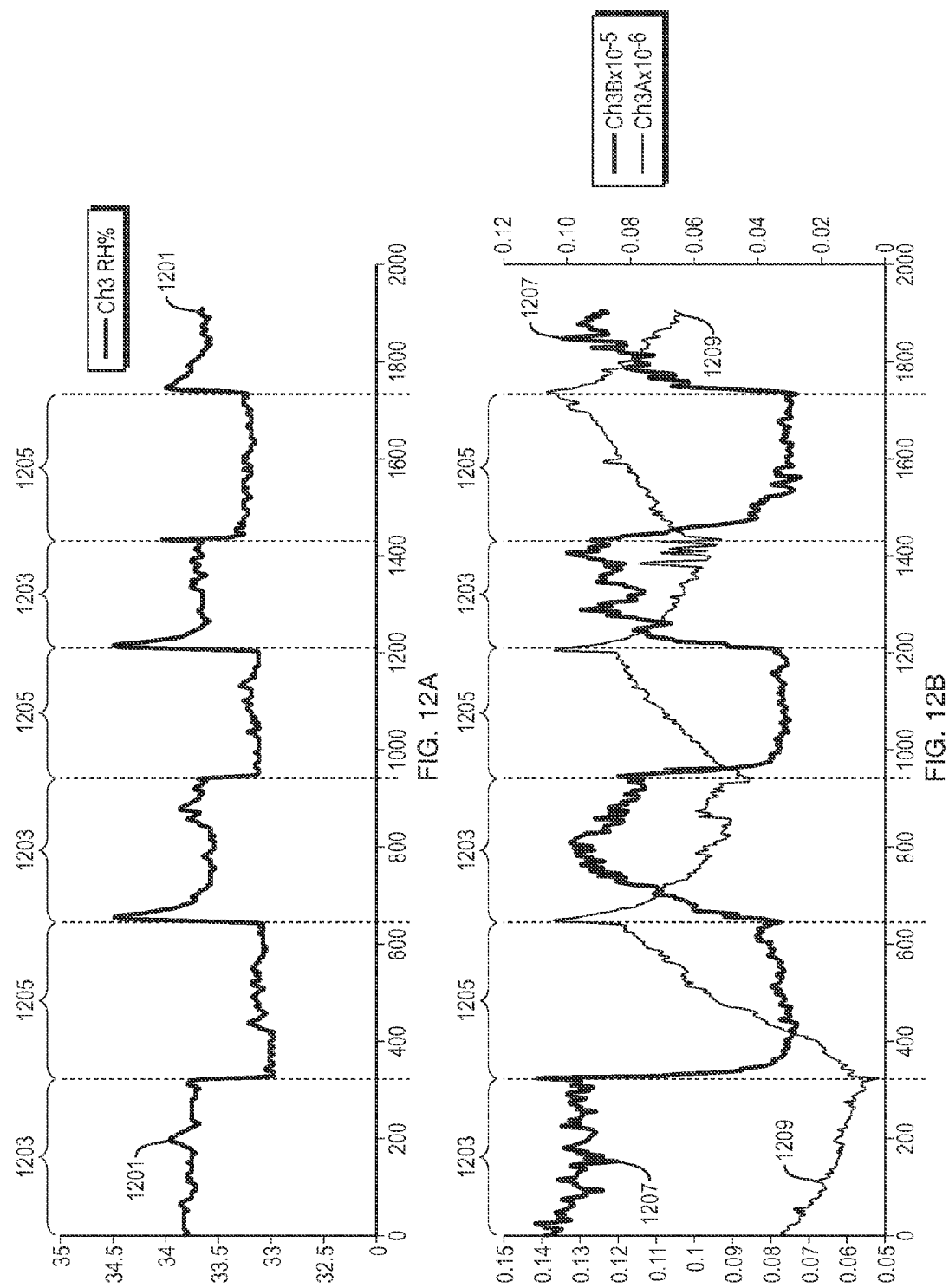

METHODS AND APPARATUS FOR ARTIFICIAL OLFACTION

RELATED APPLICATIONS

This application is a continuation of U.S. application Ser. No. 13/966,169 filed on Aug. 13, 2013 (the "'169 Application") now U.S. Pat. No. 9,140,677, which claims the benefit of U.S. Provisional Application No. 61682587, filed Aug. 13, 2012 (the "Provisional Application"). The entire disclosures of the '169 Application and the Provisional Application are herein incorporated by reference.

STATEMENT REGARDING FEDERALLY SPONSORED RESEARCH OR DEVELOPMENT

This invention was made with U.S. government support under Grant HR0011-09-C-0012 awarded by the Defense Advanced Research Projects Agency and under Grant No. N66001-10-1-4062 awarded by the Space and Naval Warfare Systems Center. The government has certain rights in this invention.

FIELD OF THE TECHNOLOGY

The present invention relates generally to artificial olfaction.

BACKGROUND

A number of misconceptions regarding biological olfaction are widely held, including by many experts in the field. These misconceptions have adversely impacted the design of electronic olfactors (commonly known as electronic noses or E-noses).

First Misconception: By determining what a volatile mixture is made of (chemical identity and accurate relative concentrations of odorants), one can predict what the mixture smells of and vice versa. This is often incorrect.

Correct: Actually, a single-molecule odorant (or set of odorants) can confer different scents (a) at different concentrations, (b) in different mixtures, (c) at different ambient humidity, temperature, or pressure, or (d) at different times post first exposure.

Second Misconception: Humans use the same "olfactory handle" when identifying odorants in different environments—analogous to specific peaks in gas chromatography mass spectrometry ("GC/MS"). This is often incorrect.

Correct: Actually, olfactory recognition handle(s) can change to dynamically adapt to recognition task requirements (and general training in one environment can carry on to a completely different environment with the specific "handle"). Sensory input is constantly being compared to memory of training experience and "attention" is focused "retroactively". This means different features of a neural activation pattern become salient in different backgrounds. Many recognizable scents (e.g. coffee, "olfactory white") do not have a well-defined molecular blueprint.

Third Misconception: The perceived scent of a combination of odorants is equal to the weighted sum of the scents of the individual odorants. This is often incorrect.

Correct: Actually, the scent of a combination of odorants can be quite different than the weighted sum of the scents of the individual odorants.

The above misconceptions form the basis of a conventional explanation of biological olfaction. Under this conventional explanation, biological olfaction consists of analytical measurement followed by pattern recognition, as follows: first steps involve molecule-identifying olfactory receptor (OR) binding events that cause conformational changes depolarizing the membrane of olfactory receptor neurons (ORNs) in the olfactory epithelium followed by local (or olfactory bulb or possibly higher brain) pattern recognition culminating in a reliably reproducible scent experience.

However, this conventional explanation describes only part of the mechanism and is only partially correct. It is incorrect to the extent it fails to recognize the importance of odorant conformation, possible mixture chemistries, agonist/antagonist effects, allosteric modulation of receptors, and complex feedback and modulation effects such as habituation, attention, generalization, etc. More importantly, this conventional explanation fails to recognize that: (1) the same single-molecule odorant can confer different scents at different concentrations, in different mixtures, at different ambient humidity, temperature, or pressure, or at different times post first exposure; and (2) the scent of a combination of odorants cannot, in many cases, be accurately predicted from the chemical identity and relative concentrations of the odorants in the combination.

Part of the reason why these misconceptions persist is because biological olfaction often appears analytical. These are many cases when the presence of a single molecule in a broad range of concentrations and against many backgrounds unambiguously dominates the odor character. Examples are vanillin, ammonia, hydrogen sulfide (rotten eggs), and skatole (feces).

However, in many cases, a scent is not defined by one unambiguously responsible molecule. For example, the scents of coffee, wine and roasted food are each formed by a combination of hundreds or thousands of odorants.

"Olfactory white" is a striking example of how the scent of a combination of odorants (a) is not necessarily defined by a single odorant in the combination, and (b) can be very different than weighted sum of the scents of the individual odorants that form the combination. Tali Weiss et al.; *Perceptual convergence of multi-component mixtures in olfaction implies an olfactory white*; Proceedings of the National Academy of Science of the United States of America, published online before print, PNAS, Nov. 19, 2012, doi:10.1073/pnas.1208110109 ("Olfactory White Paper").

In the recent Olfactory White Paper, the authors report that different mixtures of approximately 30 odorants tend to smell alike to human subjects, even though the different mixtures do not share all components in common. The different mixtures tend to converge to an olfactory white when there are at least 30 odorants in each mixture, and the odorants are non-overlapping, of equal intensity, and as a whole span olfactory space.

In the Olfactory White Paper, p. 19963, the authors observe that:

"Olfaction is . . . a synthetic rather than analytical sensory system. For example, humans are very poor at identifying components in a mixture, even when they are familiar with the components alone. Similarly, cortical patterns of neural activity induced by a mixture are unique, not a combination of neural activities induced by the mixtures' components. . . . In other words, the olfactory system treats odorant mixtures as unitary synthetic objects and not as an analytical combination of components . . . ." (citations omitted)

In biological allosteric modulation, the binding of a (partial) agonist, antagonist or modulator protein to a receptor protein in turn modulates the effect of the binding of a specific ligand to that receptor protein.

SUMMARY

In exemplary implementations of this invention, an electronic olfactor determines whether a test scent matches a positive control scent. The electronic olfactor can perform this scent matching even in the presence of a changing olfactory environment. Further, the electronic olfactor can perform this scent matching even if the positive control scent is a combination of hundreds or thousands of different odorants.

For example, the positive control scent may be the scent of a particular vintage of wine from a particular vineyard. The electronic olfactor may test samples of very similar scents (e.g., from the same vineyard for different years), and determine which of the test samples matches the positive control scent.

In illustrative implementations of this invention, no prior training is needed. In these implementations, no attempt is made to identify a single odorant (or set of odorants) that is unambiguously responsible for a scent. Instead, a computer compares the total scent pattern of a positive control sample (to which the target scent has been added during testing) with the total scent pattern of a test sample, across sweeps of many permutations of electrical inputs to scent sensors, to try to find any condition under which the total scent patterns do not match. For example, the electrical inputs may comprise source-drain voltage or gating voltage. If such a condition (where the total scent patterns do not match) cannot be found, then the computer declares a match between the test scent and target scent.

In these implementations, the artificial olfactor is well-suited for matching scents formed by a combination of hundreds or thousands of odorants. Because the artificial olfactor is comparing total scent patterns, a large number of odorants is not a problem. Indeed, the accuracy of the artificial olfactor tends to increase as the number of odorants in the mixture increases.

Furthermore, the artificial olfactor is robust in the presence of a changing olfactory environment (e.g., while moving from a florist shop, to a car garage, to a kitchen in which meat is being roasted). This is because each time an intake sample is taken, the intake sample includes the then current olfactory environment; and each time the positive control is created (by adding the target scent to the intake sample), the positive control includes the then current olfactory environment. The computer compares total scent patterns including the then current olfactory environment.

In exemplary implementations of this invention, a positive control sample flows through a first channel (Channel A) and a test sample flows down a separate second channel (Channel B). Each channel includes multiple scent sensors. In each channel, the scent sensors may be arranged in series or in parallel.

If the scent sensors in a channel are arranged in series, then the scent sensors may be sequentially tuned. Before the sample reaches the second scent sensor in the series, a computer analyzes output of the first scent sensor in the series (through which a sample is flowing or has flowed) and based on that analysis, sends control signals to adjust an electric field applied to a region in which odorant molecules in the sample interact with the second sensor. This adjustment occurs before the sample reaches the second sensor. For example, if the output of the first scent sensor indicates that the sample is outside the dynamic range of the first sensor, then the control signals may tune the second sensor so that the sample is within the dynamic range of the second sensor.

Likewise, the output of the second scent sensor may be analyzed in order to tune the third scent sensor in the series, before the sample reaches the third sensor, and so on for the remaining scent sensors in the series.

In exemplary implementations of this invention, each scent sensor is highly sensitive and responds selectively to different odorant molecules. For example, the scent sensor may comprise a FET (field effect transistor) sensor in which a high-aspect ratio (or low surface area to volume) semiconductor is coupled to a selectively "sticky" material that binds differentially to various odorant molecules. For example, the material may respond more to one odorant than to another. Also, for example, the selectively "sticky" material may comprise odorant receptors, such as G-protein coupled receptors. The semiconductors may comprise polypyrrole nanotubes, zinc oxide nanowires, or single-walled or multi-walled carbon nanotubes. The semiconductors may be stochastically deposited so that they span a gap between source and drain electrodes. These electrodes may form the fingers of an inter-digitated micro-electrode array ("IDA"). However, despite the random deposition, control of bulk properties (e.g., concentration of the semiconductors in suspension) can achieve precise reproducibility of performance of the scent sensors. The sample flows through a channel formed by the gap between the fingers of the IDA. The scent sensors for each channel are calibrated to be semi-orthogonal to each other.

In exemplary implementations of this invention, a sensor lid fits snugly over the IDA, thereby forming a low volume (e.g., 40 microliter) perfusion chamber. The cover and side walls of the sensor lid comprise a metallic material. Thus, the sensor lid functions as a Faraday cage to protect the sensor against electromagnetic interference and static electricity accumulation and discharge. Further, the sensor lid functions as a thermal mass that tends to slow down any changes in temperature in the sensor. The sensor lid may include a sensor ("T/RH sensor") that measures the temperature and relative humidity of the sample in real time as it passes through the sensor lid (e.g., immediately before or after passing through the perfusion chamber). Readings of this T/RH sensor may be used to ensure that local changes in temperature or relative humidity within the sensor do not throw off the sensor readings.

This invention is not limited to airborne odorants or scents detectable by a human. For example, in some implementations, this invention can (a) match solutes in liquid environments or (b) match odorants that are scentless to human perception.

The description of the present invention in the Summary and Abstract sections hereof is just a summary. It is intended only to give a general introduction to some illustrative implementations of this invention. It does not describe all of the details of this invention. This invention may be implemented in many other ways.

BRIEF DESCRIPTION OF THE DRAWINGS

FIG. 12A is a chart of relative humidity vs. time, showing the response of relative humidity sensor to alternating samples of ambient air and cyclohexanone.

FIG. 12B is a chart of un-normalized FET signal (current) vs. time, showing the response of two different odorant receptors to alternating samples of ambient air and cyclohexanone.

Figure 1A:
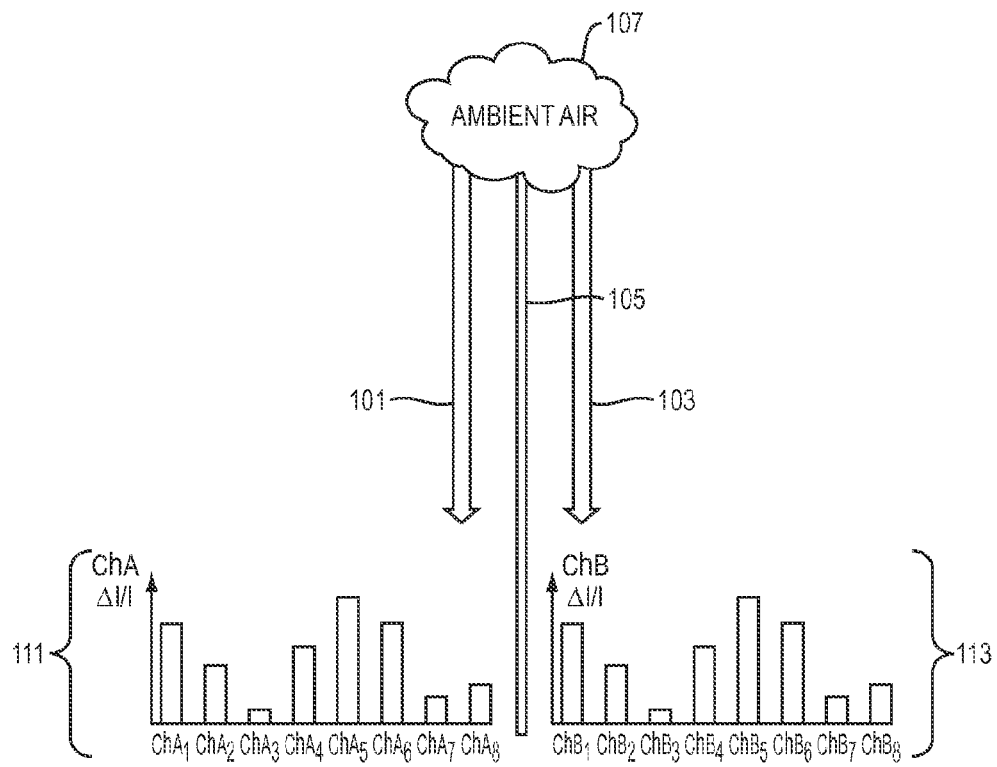
FIG. 1A is a conceptual diagram of an optional calibration step.

The above Figures show some illustrative implementations of this invention, or provide information that relates to those implementations. However, this invention may be implemented in many other ways. The above Figures do not show all of the details of this invention.

DETAILED DESCRIPTION

Scent Matching:

In exemplary implementations of this invention, an electronic olfactor determines whether a test scent matches a positive control scent. The olfactor performs the scent matching as follows:

A sample of gas to be tested (the "intake sample") is gathered. For example, the intake sample may be gathered by pulling ambient air in through an intake opening. At this time, it is unknown whether the intake sample contains a target scent.

The intake sample is divided into two separate parts, each of which consists of the same substances in the same relative concentrations. A target scent is then added to (perfused into) the first part, and is not perfused into the second part. Thus, the first part becomes a positive control sample (comprising a mixture of the positive control scent and gas from the intake sample). The second part becomes a test sample, comprising gas from the intake sample.

The two samples (positive control and test) are then run through two different channels (Channels A and B), one channel per sample. Each channel comprises multiple scent sensors. For example, each channel may comprise eight scent sensors, for a total of sixteen scent sensors in the electronic olfactor. Thus, for example: (i) the positive control sample may flow through Channel A which comprises eight scent sensors; and (ii) the test sample may flow through Channel B which comprises eight scent sensors.

The sensors within each channel may be arranged in parallel or in series. In the above example, the eight scent sensors in Channel A may be arranged in parallel or in series with each other. Likewise, the eight scent sensors in Channel B may be arranged in parallel or in series with each other.

Each of the scent sensors is configured to respond selectively to some odorants and not at all (or to a lesser extent) to other odorants.

Furthermore, the selective responses of the scent sensors differ from one scent sensor to another scent sensor. For example, one scent sensor may respond more to a first odorant and less to a second odorant, whereas another scent sensor may respond less to the first odorant and more to the second odorant.

The multiple sensors within each respective channel respond (or can be calibrated to respond) orthogonally or semi-orthogonally to a sample flowing that respective channel. In the above example, after any needed calibration: (a) the eight sensors in Channel A respond orthogonally or semi-orthogonally to the positive control sample flowing through Channel A; and (b) the eight sensors in Channel B respond orthogonally or semi-orthogonally to the test sample flowing through Channel B.

(Definition: A set of sensors responds "orthogonally" to a particular scent if only one of the sensors in the set responds to the scent and the other sensors in the set do not respond at all to the scent. Likewise, a set of sensors responds "semi-orthogonally" to a scent if one or more of the sensors in the set respond differently to the scent than the remaining sensors in the set respond to the scent. The more the responses of the respective sensors differ from each other, the more orthogonal the sensors are.)

The multiple sensors are (or can be calibrated to be) within their respective dynamic ranges (e.g., not "pegged" or saturated).

Each sensor in a channel has a corresponding sensor in the other channel, such that (after calibration, if any), both sensors in the pair have the same response to the positive control sample. For example, if the first sensor in Channel A and the first sensor in Channel B are such a pair, then (after calibration, if any) their responses to the positive control sample are substantially identical to each other.

A computer compares (1) the pattern of responses of the Channel A sensors to the positive control sample (the "Channel A pattern"), and (2) the pattern of responses of the Channel B sensors to the test sample (the "Channel B pattern").

If the computer determines that the Channel A pattern and Channel B pattern do not match, then the computer declares that the positive control scent does not match the test scent.

On the other hand, if the computer determines that the Channel A pattern and Channel B pattern match each other, then the analysis is not done. Instead, the computer outputs control signals to pair-wise allosterically modulate one or pairs of scent sensors, where for each pair, one sensor in the pair is a Channel A sensor and the other sensor is a Channel B sensor. For example: (a) a pair of scent sensors consisting of the first scent sensor in Channel A and the first scent sensor in Channel B may be allosterically modulated; (b) a pair of scent sensors consisting of the second scent sensor in Channel A and the second scent sensor in Channel B may be allosterically modulated; (c) and so on.

For example, the allosteric modulation may involve a sweep of a voltage input to a sensor. For example, allosteric modulation may comprise a sweep in which a "DC" source-drain voltage applied to a scent sensor is changed (e.g., in increments of 50 millivolts from −1.5V to +1.5V and then back down to −1.5V), while DI/I output of the sensor is measured. Or, for example, allosteric modulation may comprise a sweep in which an "AC" source-drain voltage applied to a scent sensor is changed (e.g., from 0V peak-to-peak to 3V peak-to-peak and then back down to 0V peak-to-peak), while a DI/I output of the sensor is measured. Or, for example, allosteric modulation may comprise changing the time (how long) it takes for a sweep to occur.

For example, allosteric modulation of a sensor may be achieved by varying source-drain voltage ("Vsd"), gating voltage ("Vsd"), or sweep rate for either of these voltages. "Tsweep" means the time (how long) it takes complete a sweep of an electrical parameter of a sensor.)

Furthermore, allosteric modulation of a sensor may involve multiple variables. For example, a sweep of Vsd may be done when Vg is set at a particular value, then another sweep of Vsd may be done when Vg is set at a different value, and so on.

If the rate of the sweep is too rapid, than a sensor may not have time to respond to the sweep. Therefore, in illustrative implementations of this invention, the rate of the sweep may be adjusted, including during allosteric modulation.

(Definitions:

To "allosterically modulate" a sensor measuring a sample means to significantly vary an electric field applied to a region in which odorant molecules in the sample interact with the sensor, such that the sensor's response to the sample changes significantly. For example, in a FET sensor, the electric field may in some cases be varied significantly by changing source-drain voltage, gating voltage, or rate of change of these voltages.

To "pair-wise allosterically modulate" a pair of sensors, wherein each respective sensor in the pair measures a respective sample, means to allosterically modulate the pair of sensors such that responses of the sensors to the samples undergo substantially identical variations.

To "n-wise allosterically modulate" a group of n sensors, wherein each respective sensor in the group measures a respective sample, means to allosterically modulate the group of sensors such that responses of the sensors to the samples undergo substantially identical variations.

The mere act of sending a digital signal to a sensor (e.g., a digital signal conveying an instruction or data) does not constitute "allosteric modulation" of a sensor (or "pair-wise allosteric modulation" of a pair of sensors, or "n-wise allosteric modulation" of a group of sensors"). Likewise, such a digital signal per se does not constitute such modulation.

The use of the word "allosteric" is intended merely to indicate a loose analogy between the effects of this sensor modulation and the effects of biological allosteric modulation. However, the meaning of "allosteric modulation" of a sensor (or sensor pair or set of sensors) is not limited or affected in any way (a) by comparison to biological allosteric modulation, (b) by any meaning of "allosteric", or (c) by any such analogy or lack thereof).

For example, all of the sensor pairs in Channels A and B may be allosterically modulated at the same time, or less than all of the sensor pairs in Channels A and B may be allosterically modulated at the same time.

Different permutations of electrical inputs to sensors can be used at each step of this allosteric modulation. For example, consider the permutation of all electrical inputs to all sensors in a given channel. This permutation can be changed repeatedly, using a different permutation at each step of the allosteric modulation.

Without being limited by theory, allosteric modulation of a sensor may modify the electrical output of the sensor in at least two ways: (a) by modifying the affinity of the sensor for binding with a given odorant, and (ii) by modifying the electrical output of the sensor in response to a specified interaction with an odorant. Likewise, without being limited by theory, varying an electric field applied to a region in which odorant molecules interact with a sensor may modify the electrical output of the sensor in at least two ways: (a) by modifying the affinity of the sensor for binding with a given odorant, and (ii) by modifying the electrical output of the sensor in response to a specified interaction with an odorant.

The computer continues to output control signals for allosteric modulation of sensor pairs, trying to find a permutation of electrical inputs in which the Channel A pattern and Channel B pattern are different. This allosteric modulation proceeds through multiple different permutations (the permutations being of electrical input to the scent sensors in Channels A and B). At each step, a computer compares the Channel A pattern and Channel B pattern. If the computer at any step during this allosteric modulation determines that the Channel A and B patterns do not match, then the computer declares that the positive control scent does not match the test scent.

If, after trying a certain number of multiple permutations, the computer can find no permutation in which the Channel A and Channel B pattern are different, the computer declares that the positive control scent matches the test scent.

The number of different permutations that are tested during allosteric modulation, before determining that a match exists, can be set by user input or by computer algorithm (or even changed, during testing, by user input or computer algorithm). In either case, the decision regarding how many permutations to test, before declaring a match, may take into account factors such as: (a) total cost of sensor materials used in the testing; (b) time constraints; and (c) desired level of resolution (or confidence or probability) for the match (which may vary, for example, if it is known a priori that the electronic olfactor is trying to distinguish between very similar scents or between very dissimilar scents).

The number of different permutations of electrical inputs to sensors that are tested during allosteric modulation, before declaring a match, may vary. For example, the number of permutations that are tested may be: two, three, four, five, six, seven, eight, nine, ten, between eleven and fifteen, between sixteen and twenty, between twenty-one and thirty, between thirty-one and forty, between forty-one and fifty, between fifty one and one hundred, or more than one hundred.

Calibration may be performed (or the results thereof taken into account) at any one or more times during any process described herein or for any apparatus, device, instrument or sensor described herein. For example, calibration may be performed (or the results thereof taken into account): (1) when two patterns (e.g., a Channel A pattern and a Channel B pattern) are compared by a computer; (2) when a pattern is recognized by a computer (2) before, during or after taking a sensor reading; (3) when sensor data is processed or analyzed by signal processing circuitry or by a computer; (4) during allosteric modulation of a sensor or sensors, (5) during any other variation of input to any sensor or sensor circuitry; or (6) when a computer determines whether a match exists. Also, for example: (1) any combination of different types of calibration may be performed; and (2) calibration may be applied to any aspect of a signal, including a time constant.

FIG. 1A is a conceptual diagram of an optional calibration step. In this optional step, an intake sample comprises ambient air 107. The intake sample flows into two channels: Channel A 101 and Channel B 103. These channels are separated from each other by at least a wall, barrier or other structure (e.g., 105). (The other walls of Channels A and B are not shown in FIG. 1A).

In the calibration step shown in FIG. 1A, the gas in each channel consists only of ambient air. A positive control scent is not used.

In this calibration step, a computer determines whether the pattern of sensor readings for Channel A matches the pattern of sensor readings for Channel B. Such a match would be expected, because the samples in each channel are identical (ambient air only). If the patterns of sensor readings for Channels A and B do not match each other (despite the samples in the two channels being identical), then calibration is performed until the patterns do match.

Figure 1B:
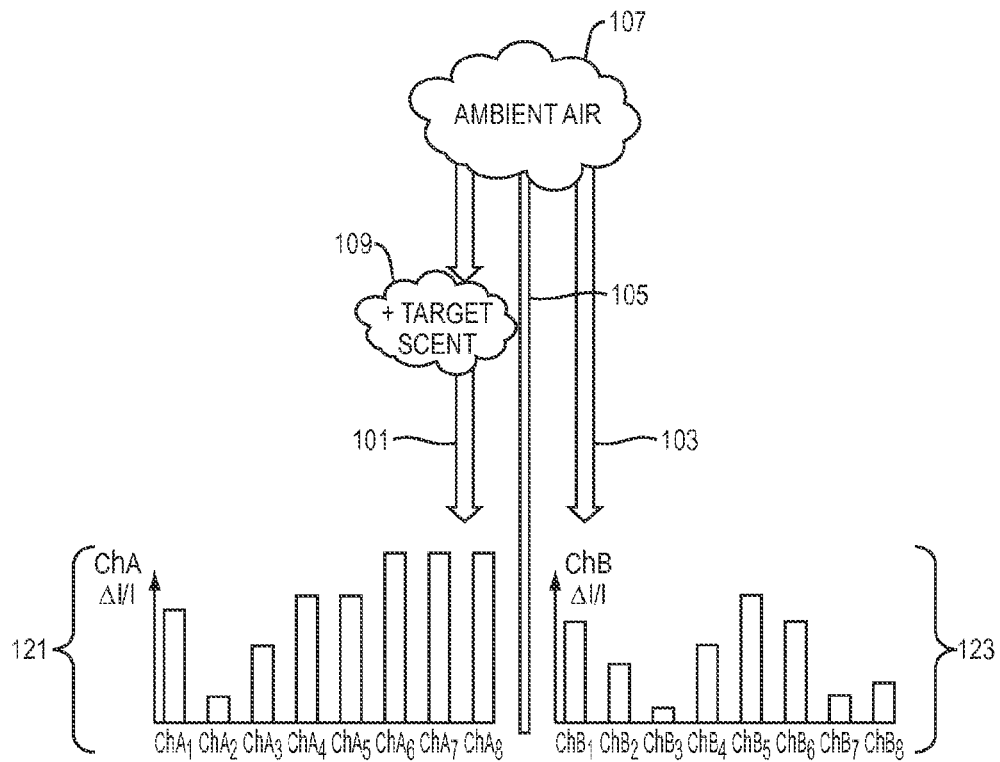
FIG. 1B is a conceptual diagram of another optional calibration step.

FIG. 1B is a conceptual diagram of another optional calibration step. In this step, an intake sample comprises ambient air 107. A positive control scent (the target scent) 109 perfuses into Channel A 101 but not into Channel B 103, thereby creating a positive control sample in Channel A but not in Channel B.

In the example shown in FIG. 1B, a computer checks whether any of the sensors are outside of their dynamic range (e.g. pegged or saturated). If any sensor is outside of its dynamic range, then that sensor is calibrated so it is within its dynamic range.

Figure 2:
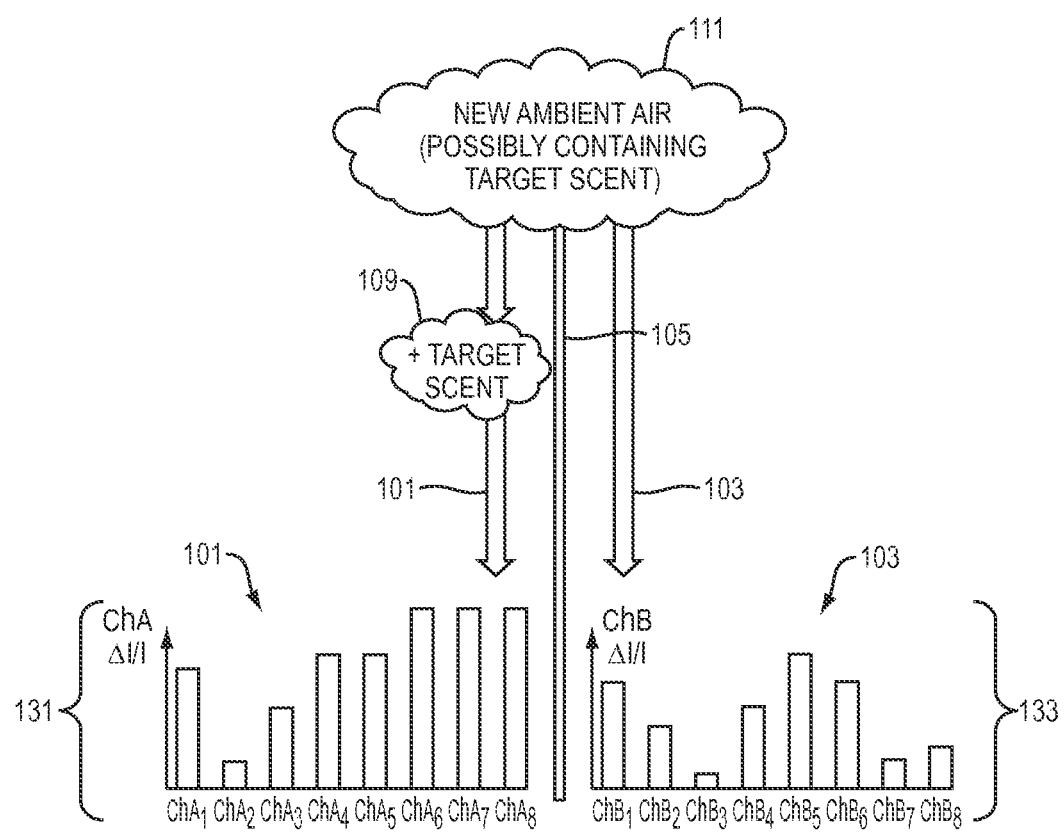
FIG. 2 is a conceptual diagram of a step in an example of scent matching.

FIG. 2 is a conceptual diagram of an example of scent matching. In this step, an intake sample comprises ambient air 111 which possibly contains a target scent. A positive control scent (the target scent) 109 perfuses into Channel A 101 but not into Channel B 103, thereby creating a positive control sample in Channel A but not in Channel B.

A computer checks whether the pattern of scent sensor readings in Channel A matches the pattern of scent sensor readings in Channel B. If they do not, then the computer determines that the scent of the positive control does not match the test scent. If the patterns match, the computer outputs control signals to allosterically modulate scent sensor pairs, to try to find a permutation of electrical inputs to sensors that causes the two patterns to not match. At each step in the allosteric modulation, a different permutation of electrical inputs to sensors is used. If, at any point during the allosteric modulation, the patterns of scent sensor readings (in Channels A and B respectively) do not match, then the computer declares that the scent of the positive control does not match the test scent. If, after trying a certain number of multiple permutations, the computer can find no permutation in which the Channel A and Channel B pattern are different, the computer declares that the positive control scent matches the test scent.

In the examples shown in FIGS. 1A, 1B and 2: Channels A and B each include eight scent sensors. The scent sensor output is calculated as $\Delta I/I$ (also called DI/I, the change in current divided by current). These sensor readings are symbolized by bar graphs 111, 121, 131 for Channel A and bar graphs 113, 123, 133 for Channel B. (The bar graphs are an oversimplification in many cases. For example, the sensor patterns that are being compared may, in many cases, be better illustrated by a curved plot for each sensor, in which the vertical axis is DI/I for that sensor and the horizontal axis is time.)

In the examples shown in FIGS. 1A, 1B and 2, the patterns match if, for each respective pair of scent sensors, the DI/I responses of the sensors in the pair match each other.

In the scent matching mode described above: (a) prior training of the electronic olfactor is not required; (b) a positive control is used in one of the two channels; and (c) electrical inputs (e.g., Vsd, Vg, or Tsweep) are repeatedly swept to try to find values that create maximal differences between DI/I responses of the control sample and the test sample. If no difference between sensor reading patterns of the two channels can be found, after a certain number of sweeps, then the electronic olfactor declares a match.

In this scent matching mode, a sample of a new/unknown scent can be used to home in on the source of that scent, or to find other scents of the same kind Consider the following example: trying to "bloodhound" a person hidden in a castle with 100 rooms. The person is wearing half a scarf and the other half of the scarf is given to the electronic olfactor as a positive control and inserted in the path of the left "nostril" of the electronic olfactor. The air in each room is sampled. Some of the rooms have very different olfactory environments (for example a kitchen in which meat is being roasted, and a musty basement). Thus, a varying olfactory background is being sampled during the test. Part of each sample flows through the left "nostril" (Channel A), where it is perfused with the positive control. The other part of the sample (which is not perfused by the positive control) comprises the test sample. Comparisons between the sensor readings for Channels A and B are made, while allosterically modifying the sensors (e.g., by changing, Vsd, Vg, or Tsweep). If, after testing a certain number of permutations of electrical inputs, no differences between the sensor readout patterns for the two channels can be found, then a match is declared.

This scent matching can be used, for example, where the original state of the sensors is not well controlled or where the sensors cannot be calibrated in low-background environments against known positives and known negatives.

If a known negative exists, it can be used to enhance accuracy and decrease false positive rates. For instance: if no known positive bladder cancer urine samples exist but a reasonable guess can be made that young patients are unlikely to have bladder cancer, their urine can be used as a tentative negative.

Figure 3A:
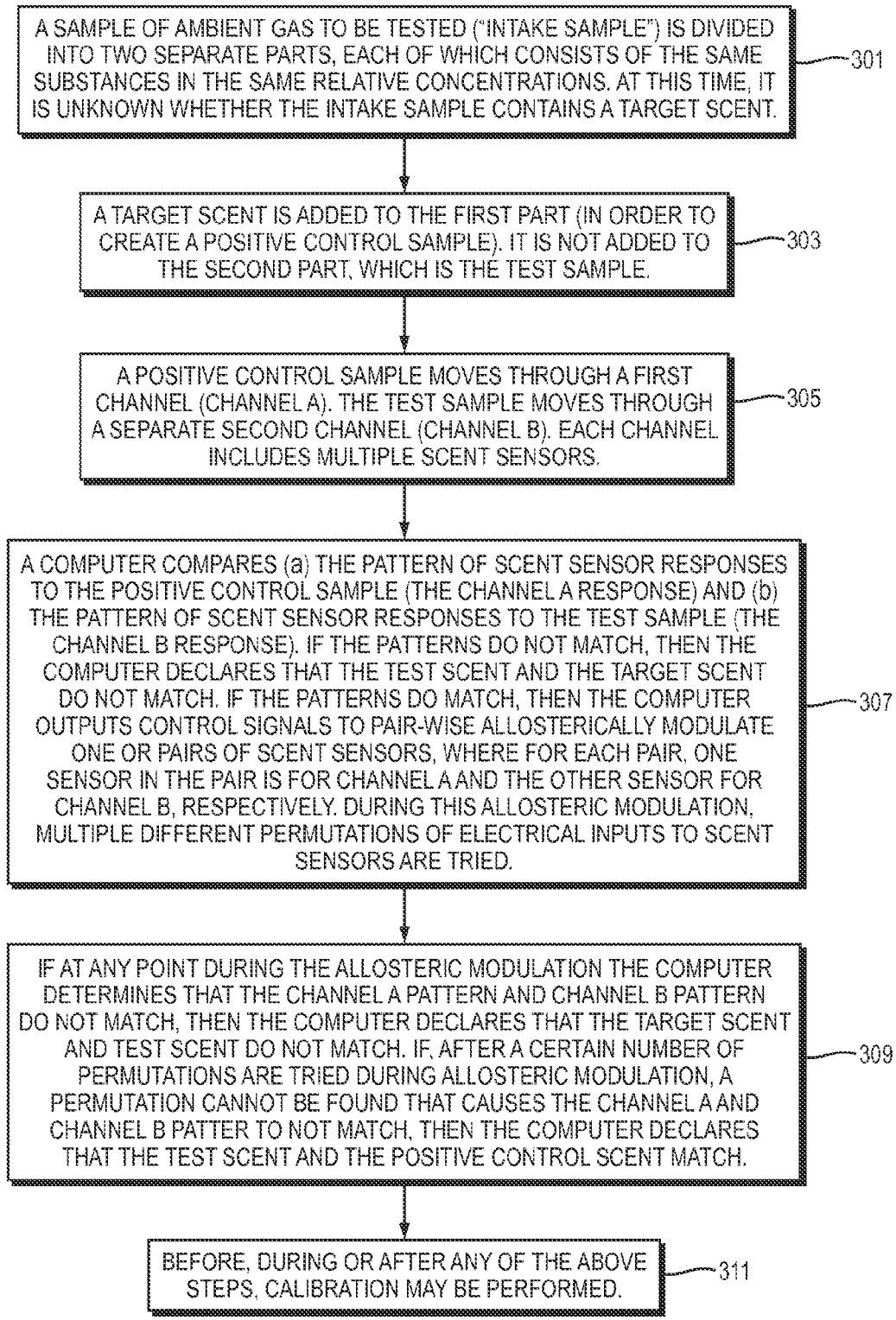
FIG. 3A is a high-level flow chart of steps comprising an example of scent matching, in which a positive control is used without prior training.

FIG. 3A is a high-level flow chart of steps comprising an example of scent matching, in which a positive control is used without prior training A sample of ambient gas to be tested ("intake sample") is divided into two separate parts, each of which consists of the same substances in the same relative concentrations. At this time, it is unknown whether the intake sample contains a target scent 301. A target scent is then added to the first part, in order to create a positive control sample, but is not added to the second part, which is the test sample 303. The positive control sample travels through a first channel (Channel A) and the test sample travels through a separate second channel (Channel B). Channel A and Channel B each include multiple scent sensors 305. A computer compares (a) the pattern of scent sensor responses to the positive control sample (the Channel A response) and (b) the pattern of scent sensor responses to the test sample (the Channel B response). If the patterns do not match, then the computer declares that the test scent and the target scent do not match. If the patterns do match, then the computer outputs control signals to pair-wise allosterically modulate one or more pairs of scent sensors, where for each pair, one sensor in the pair is for Channel A and the other sensor is for Channel B. During this allosteric modulation, multiple different permutations of electrical inputs to scent sensors are tried 307. If at any point during the allosteric modulation the computer determines that the Channel A pattern and Channel B pattern do not match, then the computer declares that the target scent and test scent do not match. If, after a certain number of permutations are tried during allosteric modulation, a permutation cannot be found that causes the Channel A and Channel B patter to not match, then the computer declares that the test scent and the positive control scent match 309. Before, during or after any of the above steps, calibration may be performed 311.

Figure 3B:
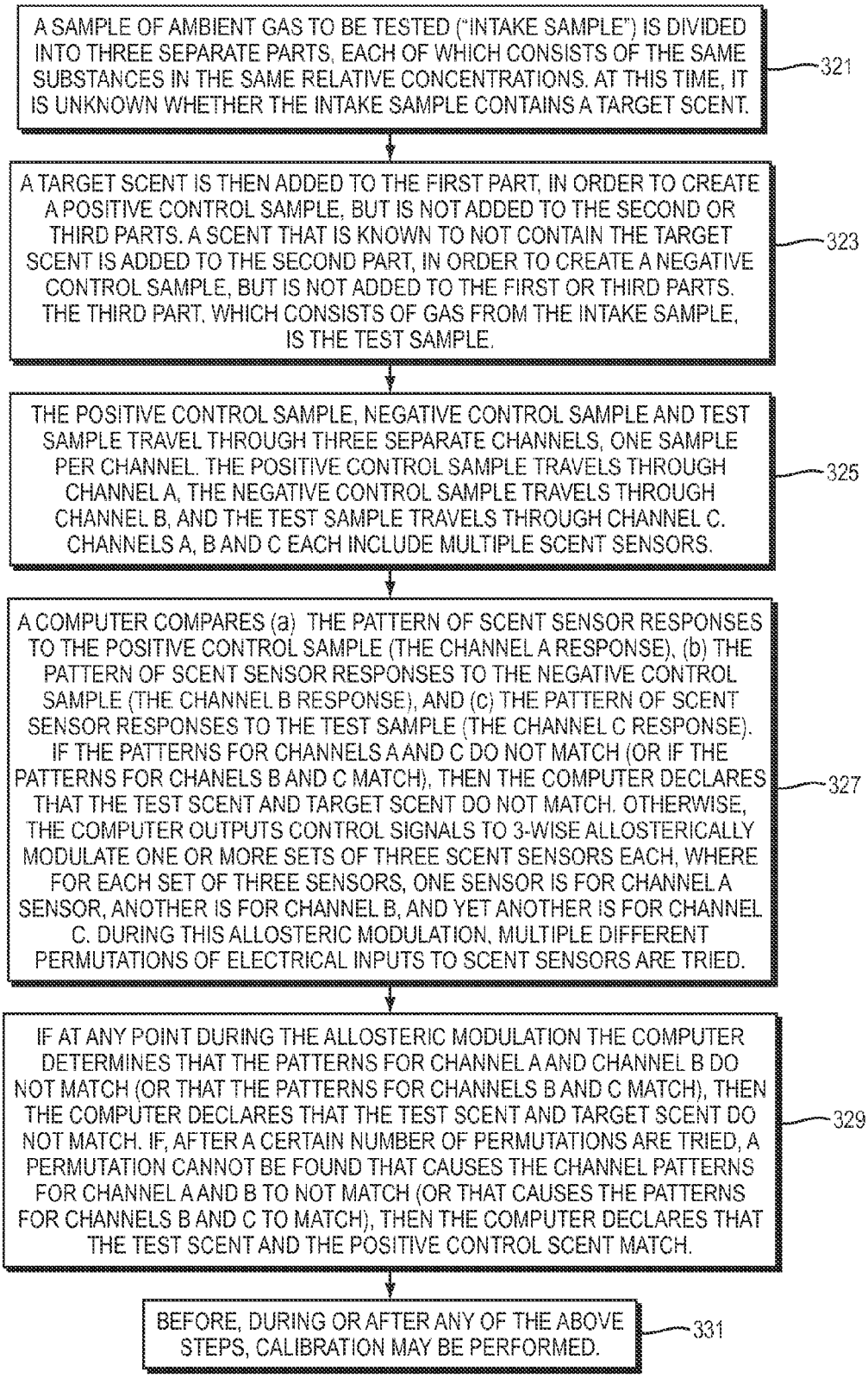
FIG. 3B is a high-level flow chart of steps comprising an example of scent matching, in which a positive control and a negative control are used without prior training.

FIG. 3B is a high-level flow chart of steps comprising an example of scent matching, in which a positive control and a negative control are used without prior training A sample of ambient gas to be tested ("intake sample") is divided into three separate parts, each of which consists of the same substances in the same relative concentrations. At this time, it is unknown whether the intake sample contains a target scent 321. A target scent is then added to the first part, in order to create a positive control sample, but is not added to the second or third parts. A scent that is known to not contain the target scent is added to (perfused into) the second part, in order to create a negative control sample, but is not added to the first or third parts. The third part, which consists of gas from the intake sample, is the test sample 323. The positive control sample, negative control sample and test sample travel through three separate channels, one sample per channel. The positive control sample travels through a first channel (Channel A), the negative control sample travels through a second channel (Channel B), and the test sample travels through a third channel (Channel C). Channels A, B and C each include multiple scent sensors 325. A computer compares (a) the pattern of scent sensor responses to the positive control sample (the Channel A response), (b) the pattern of scent sensor responses to the negative control sample (the Channel B response), and (c) the pattern of scent sensor responses to the test sample (the Channel C response). If the patterns for Channels A and C do not match (or if the patterns for Channels B and C match), then the computer declares that the test scent and target scent do not match. Otherwise, the computer outputs control signals to 3-wise allosterically modulate one or more sets of three scent sensors each, where for each set of three sensors, one sensor is for Channel A, another is for Channel B, and yet another is for Channel C. During this allosteric modulation, multiple different permutations of electrical inputs to scent sensors are tried 327. If at any point during the allosteric modulation the computer determines that the patterns for Channel A and Channel B do not match (or that the patterns for Channels B and C match), then the computer declares that the test scent and target scent do not match. If, after a certain number of permutations are tried, a permutation cannot be found that causes the Channel patterns for Channel A and B to not match (or that causes the patterns for Channels B and C to match), then the computer declares that the test scent and the positive control scent match 329. Before, during or after any of the above steps, calibration may be performed 331.

In an alternate approach, scent matching can be performed without using a positive control or negative control to perfuse a channel during a test. This alternate approach requires a training set, and is preferably done in a "big data" setting where sensors across different electronic olfactors are calibrated with each other.

Figure 3C:
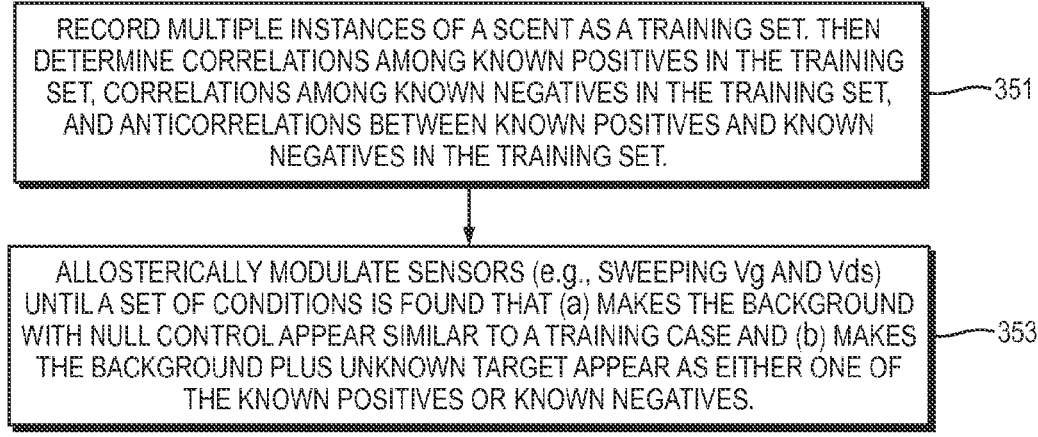
FIG. 3C is a high-level flow chart of steps comprising an example of scent matching which requires prior training.

FIG. 3C is a high-level flow chart of steps comprising an example of this alternate approach. Multiple instances of a scent are recorded as a training set, then correlations among known positives in the training set, correlations among known negatives in the training set, and anticorrelations (negative correlations) between known positives and known negatives in the training set are determined. 351 For example, many bladder cancer positive urine samples from many patients can be recorded in hospitals. Then handles of the "cancerness" scent character can be identified as useful in different environments (1) by correlations between known positives under substantially the same conditions (e.g., when the known positives are tested with sensors with substantially identical permutations of electrical inputs during allosteric modulation), (2) by correlations between known negatives under substantially the same conditions (e.g., when the known negatives are tested with sensors with substantially identical permutations of electrical inputs during allosteric modulation), and (3) by anti-correlations between a positive sample and a negative sample. For example, such anti-correlations may be bound by using a positive control for one channel and a negative sample for the other channel, or by using the positive and negative samples in one channel sequentially while leaving the other channel open to ambient air. Thus a set of "signature" changes in the cross-correlation of DI/I values can be recorded as a multi-variable function of Vsd, Vg, Tsweep, temperature, humidity, and known null background.

In this alternate approach, instead of frequently comparing to a known positive and having the advantage of seeing how the known positive looks as the environment changes, the scent matching algorithm can try to find a set of conditions that reproduces a signature training positive handle that works well on top of an immediately previous background plus null control. (Null control means that neither a positive control nor a negative control is added). This can be done by allosterically modulating sensors (e.g., sweeping Vg and Vsd) until a set of conditions is found that (a) makes the background with null control appear similar to a training case and (b) makes the background plus unknown target appear as either one of the known positives or known negatives 353. Since here both channels are exposed to same signal they can optionally double up for "voting" instead of differential detection.

This invention is not limited to any particular approach to dividing an intake sample into different parts. For example, a single intake opening can be used to draw ambient air into a tube that divides (optionally, with a valve) into separate tubes. Or, for example, the intake sample may comprise a homogenous mass of gas external to the electronic olfactor, which is brought into the electronic olfactor using two separate intake openings, one for each separate channel.

In each case of scent matching in this invention, any pattern-recognition software may be used to determine whether patterns of sensor readings for one channel match patterns of sensor readings for another channel. (It is believed, however, that how the results of that pattern recognition are used in this invention—e.g., in the course of allosteric modulation to try to find a permutation of electrical inputs for which the sensor patterns do not match—is novel.)

For example, any one or more of the following conventional pattern recognition algorithms may be employed (to determine whether patterns of sensor readings for one channel match patterns of sensor readings for another channel): a Bayesian network, radial basis function, regression model (e.g., linear regression model), sequential minimum optimization, a nearest neighbor algorithm (e.g., a nearest neighbor algorithm that learns rules), an entropic distance algorithm, a voting algorithm, a tree model (e.g., a partial decision tree model), or a compressive sensing of sparse signal (or approximately sparse signal) algorithm.

In each case of scent matching in this invention, a computer can declare a match between a first and second scent, even though un-calibrated sensor readings for the two scents are different. When determining whether a match occurs: (a) any and all types of calibration may be employed; or (b) results of any and all types of calibration may be taken into account.

For example: (a) the calibration may comprise applying a normalization or scaling factor that is either constant or predictably variant, and (b) if signals are substantially identical after this calibration, the computer may determine a match. For example, if the DI/I for Channel A saturates at twice the amplitude and half the time it takes for the same shape signal to be observed at Channel B, then a computer may (after applying a normalization or scaling calibration) determine that a match occurs.

Furthermore, in each case of scent matching in this invention, a computer may declare a match between scents which are not identical (even after calibration) if sensor readings for the two scents (after calibration) are sufficiently similar under the algorithm which the computer is performing.

For example, consider what would happen in FIG. 1 if the ambient air contained the target scent. At any given time, the two channels (one with the positive control sample and one with the test sample) might have different effective concentrations of the target scent, depending on volatility, initial concentration and nature of the target scent. In that scenario, the effective concentration of target scent in the positive control sample may be greater than, less than, or equal to the concentration of target scent in the test sample. This may cause the patterns of sensor readings of the two channels, to appear very similar, except that amplitude of all or part of the pattern may vary from channel to channel. In that case, a pattern matching algorithm may declare a match even though the patterns are not identical.

To facilitate matching (and to avoid false negatives) in this scenario, electrical inputs (e.g., Vg and Vsd) may optionally be frequently sampled so that signals are dynamically compared over a time window and trends towards matches recognized. For instance if Channel A signal at time=t1 when positive control was fresh looks substantially identical to signal in Channel B at some t2 when positive control has weakened and ChA saturated but actual target presents at full-concentration, then an "inverted" correlation between pattern of [ChA(t1) & ChB(t1)] and [ChB(t1) and ChB(t2)] may be observed and can be used to call a positive match. The t1-t2 window can be made as large as needed for a given application.

In some embodiments of this invention, test samples are taken frequently in real time, with real time surveillance for the odorant or target contaminant or compound(s). In some embodiments, whether or not samples are taken frequently in real time, sensors are not flushed between test samples.

The ability of the computer to declare a match is subject to all applicable requirements of the scent matching algorithm, including any requirement to perform allosteric modulation before declaring a match.

Scent matching in this invention is different from, and has many advantages over, conventional E-noses.

Consider, for example, a conventional E-nose comprising a GC/MS (gas chromatography/mass spectrometry) apparatus. The GC/MS E-nose analyzes an intake sample to determine the chemical identity and relative concentrations of at least some of the sample's component substances. The GC/MS E-nose requires prior training with the target scent—e.g., in order to try to identify characteristic peaks of a molecule that is unambiguously responsible for the target scent.

Or consider, for example, a conventional E-nose comprising an array of semi-orthogonal sensors (a "conventional arrayed E-nose"). This conventional arrayed E-nose is configured to try to find a characteristic signal that: (a) identifies an odorant molecule(or set of odorant molecules) that is unambiguously responsible for the target scent; (b) is buried in the total pattern of sensor readings from the array, and (c) and remains the same (after baseline adjustments) in different olfactory environments.

Both the conventional GC/MS E-nose and this conventional arrayed E-nose have at least the following problems: (a) they require prior training; and (b) even if they can identify an odorant molecule in the sample, there is no guarantee that the scent of the test sample is determined by that molecule. Further, even if the GC/MS E-nose could identify all of the odorant molecules in the sample and their relative concentrations, there is no guarantee that the scent of the test sample is determined by the weighted sum of the scents of the odorant molecules. These two conventional E-noses can identify a scent, if it is created by an unambiguously responsible molecule (e.g. vanillin), in a static and low-concentration olfactory environment. However, these two conventional E-noses are not well-suited for trying to match scents formed by a combination of hundreds or thousands of odorants (such as the scents of coffee, wine, or roasted food) and tend to be overwhelmed by a changing olfactory environment.

In contrast, in many illustrative implementations of this invention, no prior training is needed. In these implementations, no attempt is made to identify a single odorant (or set of odorants) that is unambiguously responsible for a scent. Instead, a computer compares the total scent pattern of a positive control sample (to which the target scent has been added during testing) with the total scent pattern of a test sample, across a scan of many permutations of electrical inputs to scent sensors, to try to find any condition under which the total scent patterns do not match. For example, the electrical inputs that are swept may comprise source-drain voltage or gating voltage. If such a condition (where the total scent patterns do not match) cannot be found, then the computer declares a match between the test scent and target scent.

In these implementations, the artificial olfactor is well-suited for matching scents formed by a combination of hundreds or thousands of odorants. Because the artificial olfactor is comparing total scent patterns, a large number of odorants is not a problem. Indeed, the accuracy of the artificial olfactor tends to increase as the number of odorants in the mixture increases.

Furthermore, the artificial olfactor is robust in the presence of a changing olfactory environment. This is because each time an intake sample is taken, the intake sample includes the then current olfactory environment, and each time the positive control is created (by adding the target scent to the intake sample), the positive control includes the then current olfactory environment. The computer compares total scent patterns including the then current olfactory environment.

Figure 4:
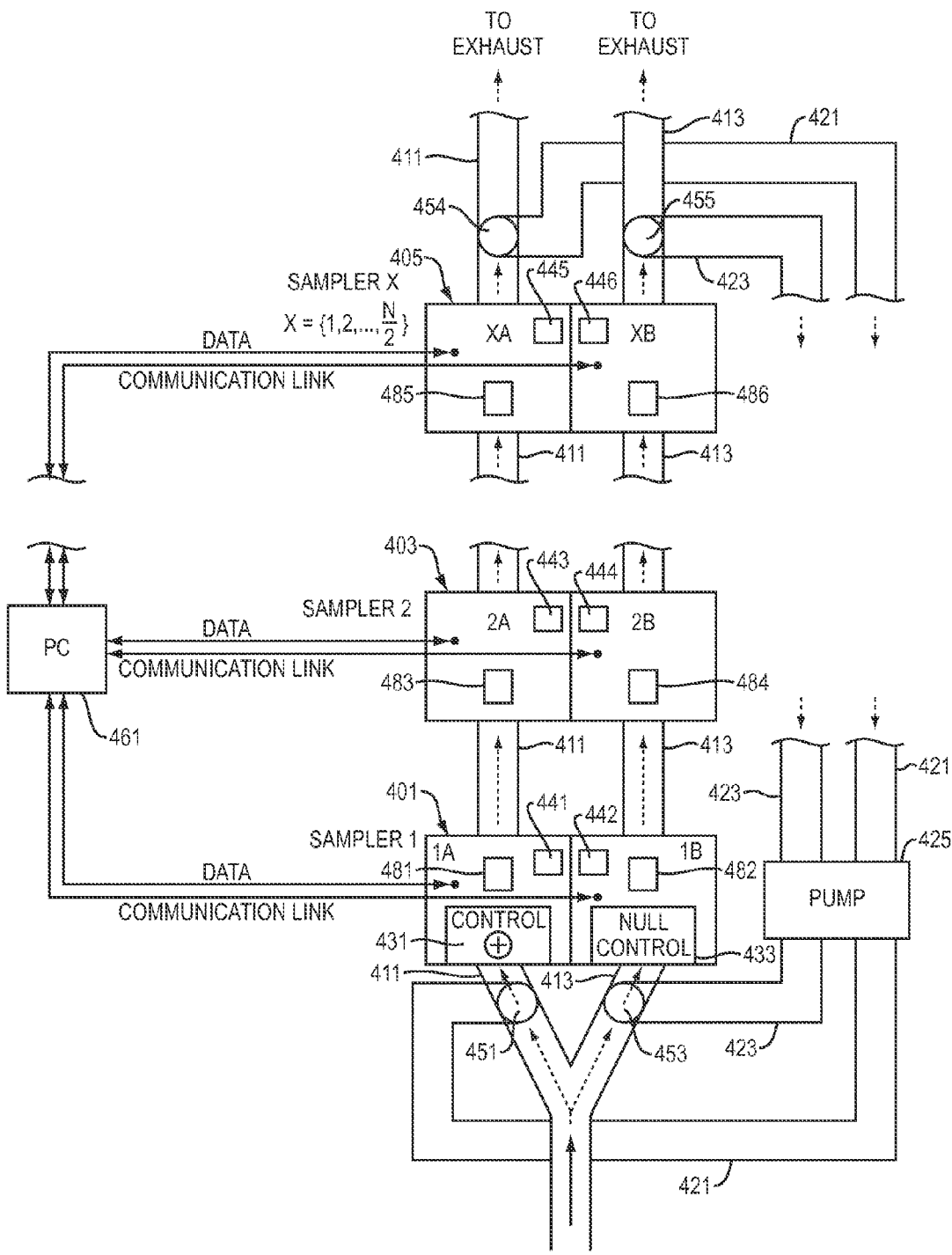
FIG. 4 is a high-level diagram of a two-channel sensor system, in which each channel flows through a series of multiple sampler heads.

Sequential Tuning of Sensors:

FIG. 4 is a high-level diagram of a two-channel sensor system, in which each channel flows through a series of sampler heads. In FIG. 4, the sensor system includes two channels (Channel A 411 and Channel B 413), N sampler heads, and X=N/2 samplers (e.g., 401, 433, 405). A positive control sample flows through Channel A and a null control sample flows through Channel B. The positive control sample may be formed by perfusing a target scent 431 into ambient air that is entering the sensor system through tube 411. Here, the null control sample consists of only ambient air that has been brought into the sensor system via tube 413.

Samplers 1, 2 and N/2 401, 433, 405 are shown in FIG. 4. Each sampler includes two sampler heads (e.g., Sampler 1 includes sampler heads 1A and 1B, Sampler 2 includes sampler heads 2A and 2B, and Sampler X includes sampler heads XA and XB). The samplers are each connected by a data link and communication link to a computer 461. The samplers each include two scent sensors (e.g., 481, 482, 483, 484, 485, 486) and two temperature relative humidity ("T/RH") sensors (e.g., 441, 442, 443, 444, 445, 446). There is one scent sensor and one T/RH sensor for each channel for each sampler head. The T/RH sensors are used for real-time, local monitoring of temperature and relative humidity of the sample within each sensor head, respectively. The scent sensors (e.g., 481, 482,

483, 484, 485, 486) each include a perfusion chamber (not shown in FIG. 4). The scent sensors are, within manufacturing tolerances, identical to each other. Likewise, the T/RH sensors are, within manufacturing tolerances, identical to each other.

Sequential tuning may be used with the set-up shown in FIG. 4. For example, before the positive control sample reaches the second scent sensor 483 for Channel A, a computer 461 analyzes output of the first scent sensor 481 for Channel A. Based on that analysis, the computer 461 sends control signals to adjust an electric field applied to a region in which odorant molecules in the sample interact with the second sensor 483. This adjustment occurs before the sample reaches the second sensor 483. For example, if the output of the first sensor 481 indicates that the sample is outside the dynamic range of the first sensor 481, then the control signals may tune the second sensor 483 so that the sample is within the dynamic range of the second sensor 483.

After an initial pass through the channels, the positive control sample and test sample may be sent to exhaust. Alternately, valves (e.g., 451, 453, 454, 455) may direct the samples to return, via tubes 421, 423 to the beginning of the channels for another pass through the channels. Although the tubes 421, 423 are shown as bending at right angles in FIG. 4, they may instead bend in smooth gradual curves in order to achieve laminar flow. One or more pumps (e.g., 425) may be located at any point in the system in order to pump the samples through the system.

Instead of, or in addition to, multiple passes through the system, the sample in each scent sensor may be temporarily immobilized (e.g., by shut-off valves) and allosteric modulation of the sensors can be performed while the sample is immobilized. In that case, the sensors' responses to the sample, during multiple different permutations of electrical inputs to the sensors, can be measured while the sample is temporarily immobilized.

Figure 5:
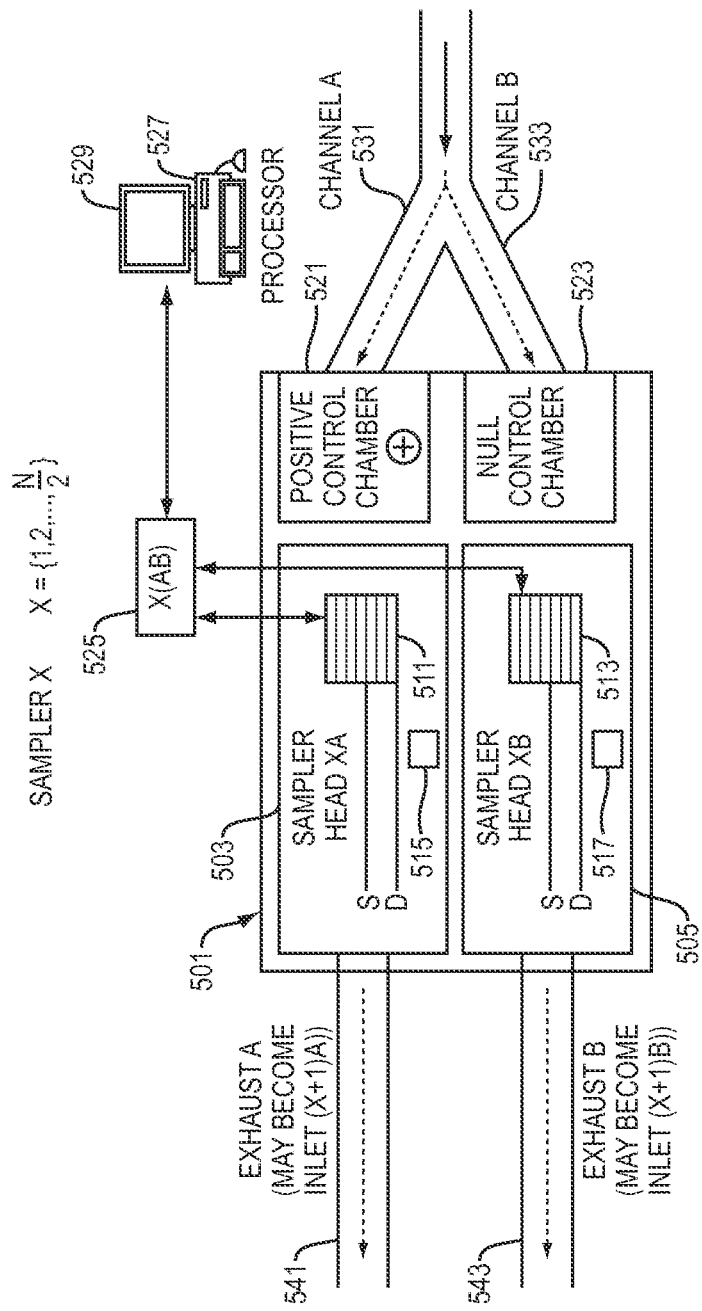
FIG. 5 shows a sampler, in this two-channel sensor. The sampler includes two sampler heads, one for each channel.

FIG. 5 shows a sampler (sampler 501, also called Sampler X) in this two-channel sensor system. The sampler 501 includes two sampler heads 503, 505, one for each channel. Each sampler head includes a scent sensor and a T/RH sensor. For example, sampler head XA 503 includes scent sensor 511 and T/RH sensor 515; and sampler head XB 505 includes scent sensor 513 and T/RH sensor 517. Channel A enters sampler head XA 503 via inlet tube 531 and exits that sampler head via egress tube 541. Likewise, Channel B enters sampler head XB 505 via inlet tube 533 and exits that sampler head via egress tube 543. Egress tubes 541, 543 may go directly to exhaust or may instead become inlet tubes for the next sampler in the series. If sampler 501 is the first sampler in the series, then (1) in a positive control chamber 521, a target scent (positive control) may be added to (perfused into) the sample flowing in Channel A; and (2) in a null control chamber 523, nothing (a null control) is added to the sample. In most implementations, there is only one positive control chamber (or null control chamber, as the case may be) for a channel, located in the first sampler before the first scent sensor.

A computer 527 and screen 529 may provide a graphical user interface for accepting input from a human and displaying information to the human. Further, the computer 527 may receive and send data and other communications (via a link 525 onboard the sampler) to and from the sampler.

The role of the two channels may be easily switched by switching the chambers in which the positive control and null control are located and flushing the prior samples from the system.

The data collected by sampler head N is analyzed and the information pertinent to make the next board's measurement maximally useful in total scent matching is transmitted to sampler head N+1 faster than the time it takes the odorants in the air sample to move from sampler head N to sampler head N+1. Conditioning of the measurement of the (N+1)th sampler head may involve setting (N+1)th source-drain bias voltage (Vsd), gating voltage (Vg) or sweep rates (Tsweep) between maximum and minimum values of Vsd, Vg and Tsweep based on the Vsd, Vg and Tsweep values and the corresponding DI/I results for sampler head N.

This daisy-chain sequential tuning is made possible in part by fast electronics, and in part by the arrangements of the sensor sampler heads in a series manner.

Thus, in illustrative implementations, this invention includes two highly advantageous features: (1) the ability to start "rough" by setting some arbitrary Vsd, Vg and Tsweep and narrowing down to useful values dynamically; and (2) the ability to use computer-controlled valves to cause odorants to repeatedly flow around the same loop of N/2 samplers while input of external ambient air is shut off (or optionally to temporarily immobilize odorants in perfusion chambers). These features may facilitate testing in which Vsd, Vg or Tsweep values are dynamically adjusted until a match is found or it is determined there is no match.

Sensors:

It is preferable for a scent sensor to be both selective (respond differently to different odorants) and highly sensitive (respond to low concentrations).

In an illustrative embodiment of this invention, both of these goals are achieved by attaching GPCRs (G-Protein Coupled Receptors) to a FET (field effect transistor). The FET provides high sensitivity in part due to possessing a high aspect ratio (or high surface area to volume ratio) so that small perturbations to the environment directly adjacent to the surface (such as volatile molecules coming into the vicinity and interacting via electrostatic or electrodynamic fields) result in measurable changes in the charge carrying characteristics of the semiconducting substrate. The GPCRs make the sensor selective, so that it responds differently to different odorants.

Figure 6A:
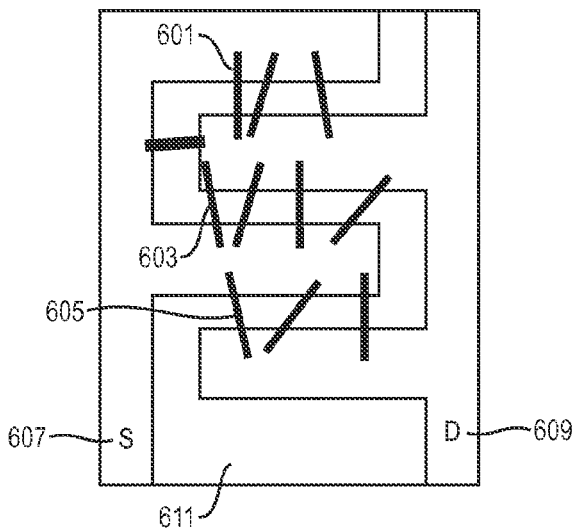
FIG. 6A shows polypyrrole (PPY) nanotubes stochastically deposited on an inter-digitated micro-electrode array.

In this embodiment, a FET comprises polypyrrole (PPY) nanotubes stochastically deposited on an interdigitated micro-electrode array (IDA). FIG. 6A shows such an arrangement. In FIG. 6A: PPY nanotubes (e.g., 601, 603, 605) are randomly deposited on an IDA. IDA finger 607 comprises a FET source, and IDA finger 609 comprises a FET drain. For a single PPY nanotube, part of the PPY nanotube may touch the source 607, part of the PPY nanotube may touch the drain 609, and part of the PPY nanotube may span a gap between the source and drain. The gap between the source 607 and drain 609 forms a channel 611 through which an odorant sample may flow. The channel is approximately 5 microns wide and approximately 150 nm deep. FIG. 6A is not drawn to scale. In practice, concentrations of PPY nanotubes are much higher than shown in FIG. 6A.

The PPY nanotubes are separately assembled using azo dye templates. Optionally, Carboxylic acid (CA) hooks may be incorporated in the PPY nanotubes to facilitate later attachment of GPCRs. For example, CA hooks can be incorporated every 15 or every 30 PPY monomers. A 40 microL drop of PPY nanotube solution may be allowed to dry on each IDA channel, resulting in a random distribution of PPYs in the channel.

In an IDA, conducting fingers etched on and separated by non-conducting glass can act as the source and drain electrodes of a FET (completed by a semiconducting bridge). The electrodes for gating voltage of the FET may be located in (a)

the ceiling of a perfusion chamber (e.g., in a sensor lid), and (b) in the floor of the perfusion chamber beneath the glass, in order to create an electrical field that is perpendicular to the ceiling and floor.

In an illustrative embodiment of this invention, a GPCR can be produced as follows: The base sequence of a GPCR gene for an olfactory receptor (OR) can be obtained from literature (e.g. the sequence for hOR17-4). Using software, codons can be modified to facilitate expression in a commercially available cell-free expression system kit (CFES). Short amino acid sequences coding for tags facilitating purification (e.g. rho- or his-) or oriented binding can be included. The gene sequence can be sent to a commercial gene-assembly facility or can be assembled in-house from oligos. The assembled gene can be used to express the GPCR in a cell-based or cell-free expression system. The GPCR can be purified using high performance liquid chromatography (HPLC). Subsequently, the GPCR can be kept soluble using commercial surfactants such as Brij35 or FC14 and can be stabilized in a buffer solution using the same surfactants or in a hydrogel using additional peptide surfactants such as A6K and V6D. For example, the GPCRs can be stabilized on the surface of the PPY nanotubes by application of the peptide surfactant RADA16 (Puramatrix™) or a hydrogel of 0.1% w/w peptide surfactant A6K or a 1:1 mixture of A6K:V6D peptide hydrogel of total 0.1% w/v.

In this embodiment, 40 microliters of a controlled concentration of PPYs suspended in ethanol solvent is pipetted on each IDA channel and the ethanol is allowed to evaporate, leaving a dry disk-shaped deposition of PPYs centered on the center of the IDA channel and of diameter smaller than the width and length of the IDA channel. GPCRs can then be attached to PPY nanotubes by depositing a 40 uL drop of buffer solution containing stabilized ORs to each channel of the IDA that has been covered with PPY solution. As a result, the GPCRs are randomly distributed on the PPY nanotubes.

Figure 6B:
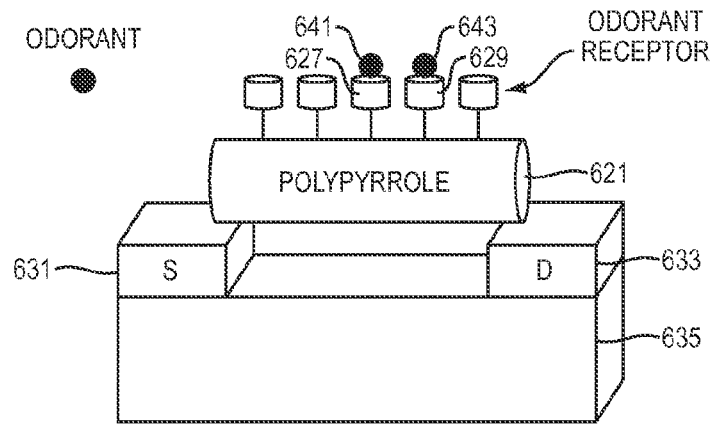
FIG. 6B shows a PPY nanotube functionalized with odorant receptor ("OR") proteins.

FIG. 6B shows an example of a PPY nanotube 621 coupled with odorant receptor ("OR") proteins (e.g., 627, 629). For example, the OR may be a GPCR. The PPY nanotube spans a gap between the source 631 and drain 633. In the example shown in FIG. 6B, odorants 641, 643 have bound to ORs 627, 629, respectively.

In this embodiment, each sensor includes two channels (e.g. one channel for measuring samples with a positive control and the other channel for measuring samples without a positive control). Each channel is formed on an IDA of conductive fingers. For example, the fingers may comprise platinum or gold. The conductive fingers of the IDA (e.g., fingers 607 and 609 in FIG. 6A) may be photolithically deposited to 5 micron thickness, 5 micron separation, 150 nm depth on passivated borosilicate glass (e.g., glass substrate 611 in FIG. 6A).

In this embodiment, control over bulk properties in liquid (e.g. concentration of PPYs, concentration of ORs) can achieve reproducibility across channels: In each channel, the PPY bridges and ORs are randomly distributed. However, because the droplet diameters are smaller than IDA area, average properties such as base resistivity of IDA are well controlled. Thus, reproducibility across channels is achieved, without using precise nano-control of placement of individual nanotubes.

In this embodiment, the FET sensor comprises an IDA sensitized with high aspect ratio semiconducting PPYs that responds differentially to different odorants based on the type and concentration of immobilized OR as well as applied bias (e.g., source-drain bias or gating bias).

In exemplary embodiments of this invention, a FET scent sensor comprises nanostructured semiconducting substrates (e.g., PPY nanotubes or ZnO nanowires) functionalized with GPCRs. For example, in a prototype of this invention, a FET sensor can measure currents induced upon exposure to odorant mixtures in the dry phase with relative humidity in the range from 0% to 100% and temperature in a range of 1° C. to 95° C.

Allowing PPY nanotubes to dry out of ethanol solution on platinum or gold IDAs and tracking DI/I creates an exceptionally sensitive gas sensor. De-sensitization by hydrogel-stabilized GPCR offers selectivity in the responses to odorants, thereby changing a sensitive gas sensor to a "nose".

In exemplary implementations of this invention: (a) Vsd (source-drain voltage) may be kept constant or swept; and (b) Vg (gating voltage) may be kept constant or swept. For example, Vsd may be kept constant while DI/I (difference in current normalized to base current) is measured. Without being limited by theory: (a) interaction between odorants and odorant receptors may affect resistance of PPY nanotubes; and (b) DI/I may correspond to changes in resistivity resulting in modulation of charge-carrying characteristics of the FET.

Without being limited by theory, "allosteric modulation" of electronic sensors (e.g. by a sweep of Vg or Vsd) may be loosely analogous to the following phenomena in the biological domain: (1) allosteric modulation of GPCR affinity and (2) different GPCR affinities conferred by small changes in the binding pocket sequence. In the exemplary implementations of this invention, the same GPCR under different bias Vsd and Vg gives different DI/I (t) characteristics for a single scent sample. This means that, within limits, the same sensor can be biased to increase resolution of detection by dynamically changing its affinity and response to odorants.

The ability to "allosterically modulate" the affinity of the individual sensors (e.g., by changing Vsd, Vg and Tsweep dynamically), significantly multiplies the resolution and usefulness of a small number of sensors to essentially act as a much larger number of sensors.

In illustrative implementations, different GPCRs may be deposited in different scent sensors, one GPCR per sensor, in order to cause the different sensors to respond different to a given odorant or set of odorants. Alternately, different concentrations or different combinations of GPCRs may be deposited in different scent sensors, in order to cause the different sensors to respond differently to a given odorant or set of odorants. Alternately, only one GPCR can be deposited in all of the sensors, and the sensors may be made semi-orthogonal by varying electrical inputs (such as bias voltages) to the scent sensors. This variation in electrical imputs to the sensors may have an effect on the scent sensors that is loosely analogous to biological allosteric modulation.

(Clarification: The phrase "one GPCR per sensor" means one GPCR folded protein sequence per sensor, although many molecules of that sequence may be deposited on a single sensor. Likewise, depositing "only one GPCR" on all sensors means depositing only one GPCR protein sequence on the sensors, although many molecules of that same protein may be deposited on the sensors.)

In some embodiments, resolution may be enhanced by the manner in which GPCRs are deposited on sensors. Consider an example where a first GPCR and a second GPCR are known to respond in opposite directions to a target scent. In this example: (a) only the first GPCR is deposited on a first sensor; (b) only the second GPCR is deposited on a second sensor; and (3) both the first GPCR and second GPCR are deposited on a third sensor. The relative concentrations of the first and second GPCRs on the third sensor are such that their responses to the particular target scent cancel out at specified relative concentrations of the first and second GPCRs. This arrangement creates an extraordinarily sensitive sensor (loosely analogous to a Wheatstone Bridge circuit), for determining whether a test scent matches that particular target scent.

For example, in the case of two very similar scents (e.g., two different vintage wines of the same varietal and vineyard, or an authentic and a counterfeit leather handbag), the overall scent character would likely be similar over a wide range of handles so distinguishing the two would likely depend on fine variations in total scent response. In such cases, it would be advantageous to balance the third sensor for the positive control such that the DI/I responses of the mix of GPCRs are such that total DI/I is zero for the positive control (say the authentic product or one of the vintages) expecting it to deviate from zero for the other instance of the closely related scent.

Figure 6C:
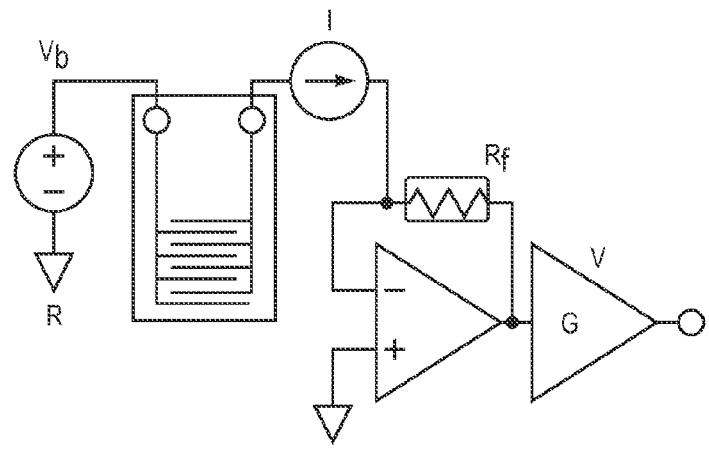
FIG. 6C shows a high level diagram of signal amplification and acquisition circuitry.

FIG. 6C shows a high level diagram of signal amplification and acquisition circuitry for an interdigitated scent sensor, in an illustrative embodiment of this invention.

In an illustrative embodiment of this invention, an artificial olfactor employs eight independently addressable (series or parallel) test chambers with two independently or commonly addressable channels of low volume. Temperature and relative humidity of carrier stream is tracked online independently in each chamber. Measurement volumes are minimal (~40 microliters), enclosures are made of polished stainless steel, and samplers can be addressed by independent electronics boards. This setup allows quick evacuation and exchange of odorants and on-line real-time analysis of changes in electrical currents induced by changes in temperature and relative humidity (which to first order may account for general FET signals often mistakenly attributed to specific effects in sensitized semiconductor "nose" settings).

In this illustrative embodiment, a DC or AC bias voltage is applied between source and drain (Vsd). Vsd voltages from +/−20 mv up to +/−2.2V have been tested in a prototype and best responses were found to be in the 0.5-1.5V range but ranges up to 10V can be useful in this embodiment. Vsd can be kept constant (DC) or oscillate (AC) with a period Tsweep. As different gaseous samples are introduced into test chambers the ratio of the change in current over the baseline current (DI/I) fitted to a straight line and calculated over a window of time is tracked in real time.

Figure 7:
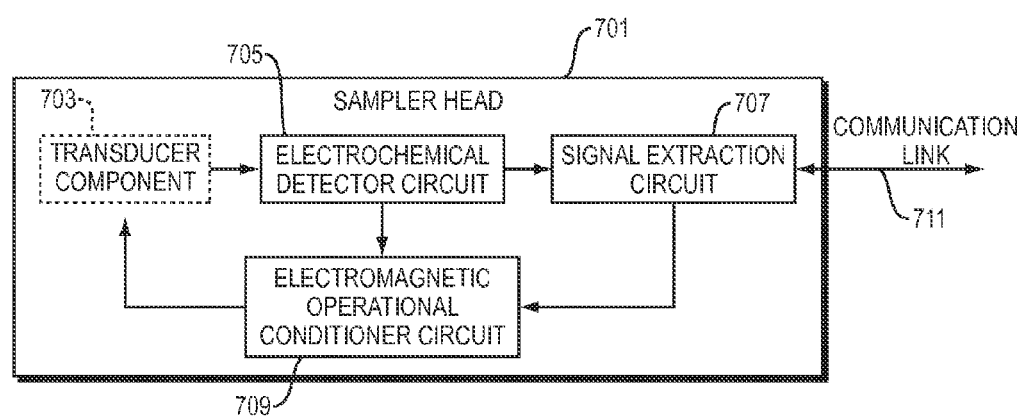
FIG. 7 shows a high-level block diagram of a sampler head.

FIG. 7 shows a high-level block diagram of components of a sampler head. The sampler head 701 comprises a transducer component 703 (e.g., a PPY nanotube functionalized with GPCRs) which undergoes a change in electrical parameter upon interaction with odorant molecules, an electrochemical detector circuit 705 for detecting the change in electrical parameter, a signal extraction circuit 707 for extracting a signal from the output of the detector circuit, and an electromagnetic operational circuit conditioner 709 for changing electrical inputs (e.g., bias voltage) to the transducer component 703. The sampler head 701 is linked to external devices (e.g., processors or other detection channels) via a communication link 711, which may be either wired or wireless.

Figure 8:
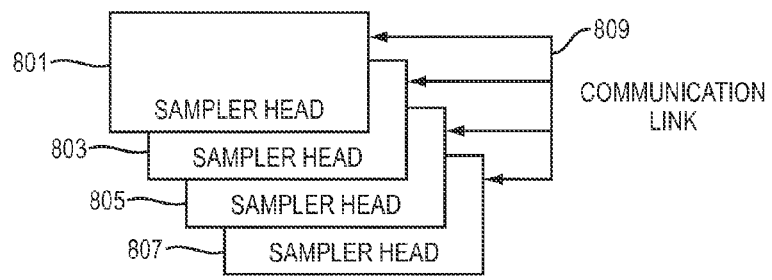
FIG. 8 shows bi-directional communication links.

Multiple sampler heads (e.g., 801, 803, 805, 807) may be linked to each other by bi-directional communication links (e.g., 809), as shown in FIG. 8.

The following is a description of a scent sensor module ("Sensor Module") and associated circuitry, in an illustrative embodiment of this invention.

The Sensor Module includes a chemo-resistance signal conditioning system that is used to capture and digitize information from a set of specialty current mode sensors.

The Sensor Module comprises N=16 sensors (each sometimes called a "sampler head"). There are N/2=8 "samplers". One sampler comprises two sampler heads. For example, one sampler head in a sampler may be used to measure scent in one test channel, and the other sampler head in the sampler may be used to measure scent in another test channel.

In each sampler in this Sensor Module, two test channels flow through two perfusion chambers (one chamber for each channel.). The perfusion chamber is open at each end, allowing the sample to flow through it. For each perfusion chamber, a scent sensor is coupled to a lock-in amplifier, and additional sensors measure relative humidity and temperature of the sample in the chamber in real time.

In this Sensor Module, the flow of samples may be in either direction. The enclosures, other hardware and software can handle flow in either direction. However, once a direction is established in a test, it is preferable to keep it that way for the remainder of that test, in order to not back-contaminate samples, etc.

Figure 9:
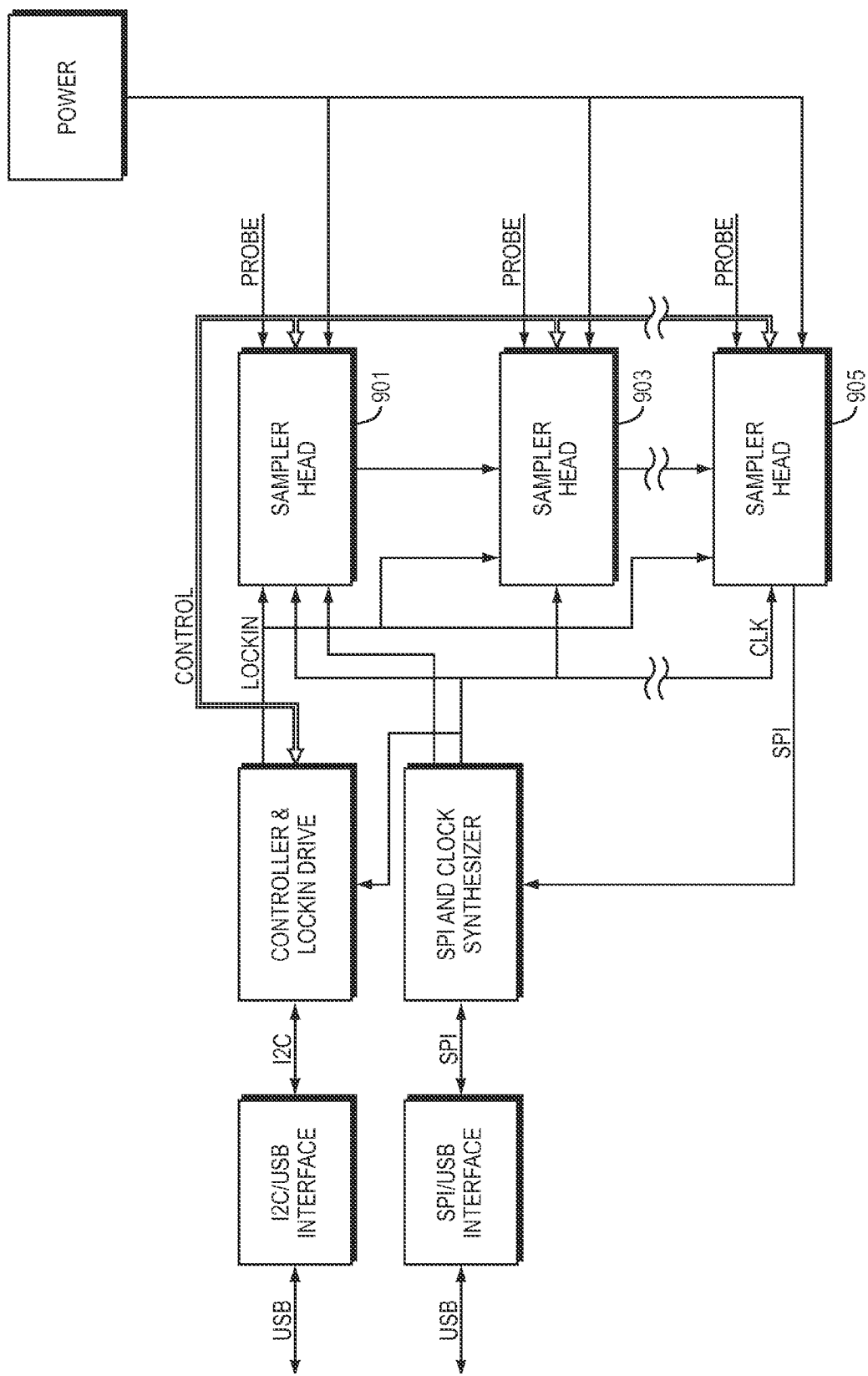
FIG. 9 shows a high-level block diagram of circuitry for multiple sampler heads.

FIG. 9 shows a high-level block diagram of circuitry for multiple sampler heads (e.g., 901, 903, 905), in this Sensor Module. Each sampler head measures scent in a probe (perfusion chamber). Each sampler head contains a series of amplifiers that create a 1×, 10× and 100× signal levels that are simultaneously sampled with an internal 24 bit SPI type ADC. In addition to the 3 simultaneous signal readings, a reference drive signal is also sampled. These sampled values are buffered into an onboard FRAM, then streamed to an external PC through USB interface.

Figure 10:
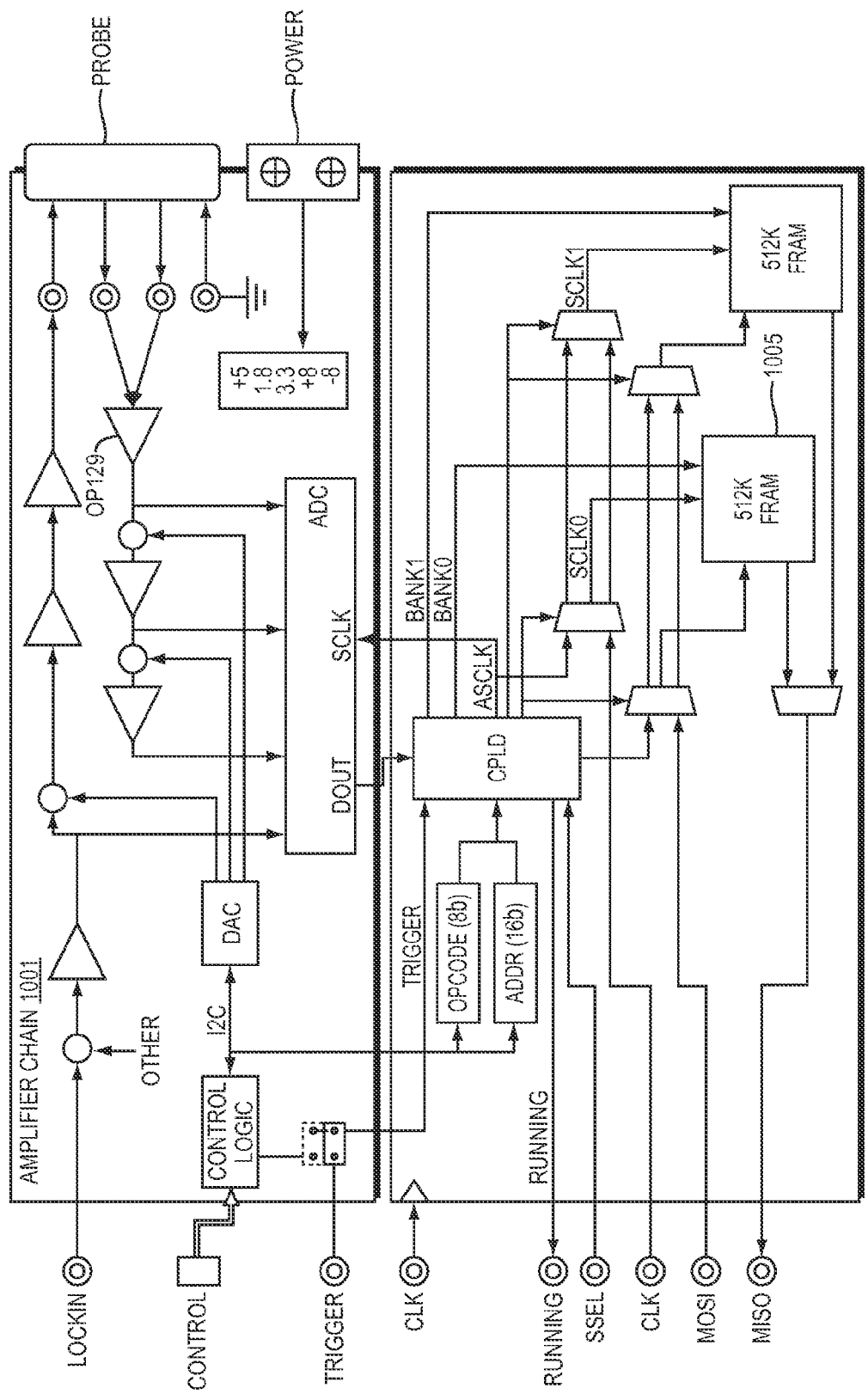
FIG. 10 shows a high-level block diagram of a sampler head with ADC and data memory.

FIG. 10 shows a high-level block diagram of a sampler head with ADC and data memory, in this Sensor Module. An amplifier chain 1001 includes a series of amplifiers that are used to condition the sensor signal and drive the 4 channel ADC. On-board logic is used to synchronize and trigger the sampling system. All static control is managed through an I2C interface. The maximum bit rate of the I2C is 400 Khz. High speed data streaming is accomplished through a Serial Peripheral Interface (SPI). The maximum data rate of the SPI shown below is 40 M bits/second. The ADC sampling clock, derived from the SPI master clock, runs at 20 Mhz. Since the ADC runs at 64× oversampled, the actual maximum ADC sample rate is 312.5 K samples/sec. This clock rate is adjustable through an API call to the SPI-USB interface.

In this Sensor Module, a probe attaches to the sensor and provides a stimulus for driving a test signal. The test signal may be controlled by either the internal DAC channel or an external LOCKIN input.

A trigger is used to synchronize several sampler heads. The +/−10 volt power supplies are connected through the terminal block screw terminals on the PCB. The sampler head produces its own internal regulated voltages; +8, +5, −5, −8, +1.8 and +3.3 volts DC. The regulators are all linear devices to eliminate potential switching noise.

In this prototype, the input amplifier is an OPA129E low noise JFET amplifier with ultra-low input bias conditions.

Secondary stages do not contribute to the measurement noise as long as the first stage has enough gain to produce a SNR above the ADC resolution. In this prototype the ADC resolution is 24 bits.

In this prototype, the output impedance of the sensor is 1 Giga-ohm.

The noise is dominated by the input noise current across the output impedance of the sensor.

The PCB input layout is sensitive to noise and leakage current. To ameliorate this effect the PCB has a guard ring to remove stray leakage and a slotted PCB to prevent differential leakage across the inputs.

The OPA129 is packaged with connections to handle the guard ring on pins 1, 4 and 8. There are 4 connections for "POGO PINS" that allow probing to either the inner or outer pads of the sensor.

The gain bandwidth product of the amplifier along with its gain setting and compensation capacitor limits the bandwidth of the amplifier. The signal bandwidth of the sensors is below 100 Hz. On the other hand, it is desirable to provide a higher bandwidth to enable a software lock in amplifier path for processing the signal above the noise corner of the amplifier. A trade-off between gain and bandwidth may be chosen to allow a mid band lock-in bandwidth of at least 1 KHz.

In this Sensor Module, the amplifier includes a differential buffer that is used to drive the ADC input. Because the ADC is a switched capacitor oversampled system, it has an irregular input impedance that depends on the sampling frequency. In addition, the sampling capacitors inside the ADC device require a drive large drive current to ensure settling of the sample values before each conversion. The input impedance is determined by a number of factors. The ADC differential drive is accomplished with a high speed single ended to differential drive circuit.

This amplifier features internal matched resistors which eliminate the need to hand-sort matched precision resistors to set up a matched differential pair. In addition it provides excellent drive capability to the ADC input. Since there are 4 channels used on the ADC, there are 4 drive buffers. Every drive buffer output is terminated by 50 ohm series resistors to reduce board noise by reducing load current spikes.

In this Sensor Module, there are 2 additional gain stages in the sampling head. Each stage has a gain of 10×. These stages consist of the LTC2052 low noise chopper stabilized quad amplifiers. The quad package provides a compact footprint that allows this amplifier to be used for the distributed gain stages that produce gains of 10×and 100×. The output drive is capable of handling capacitance loads up to 10 pF with 2 mA of drive current.

In this Sensor Module, the normal operation of the sampling head is to allow the amplifier stages to saturate if the signal is over-range. The LTC2052 amplifiers will recover slowly with this saturation so an output clamping technique is used to limit the output to +/−4 Volts. This is accomplished with the LT1498 high output drive amplifiers, shown below. With a gain bandwidth product of 10 MHz, there is ample bandwidth to ensure these gain stages do not limit the system bandwidth.

In this Sensor Module, the input offset for each stage is controlled at the reference terminal by the DAC control output. During a sample run the input offset can be fixed to allow range shifting across the amplifier chain. The input offset and drive signal for the sensor is controlled via a 10 bit DAC. The quad DAC (Texas Instruments DAC6573) drives the offset input to the $2^{nd}$ and $3^{nd}$ stage gains as well as the voltage drive for the sensor. Although the control-DACs are only 10 bits, the monotonicity, differential and integral nonlinearity can be characterized through the use of the $4^{th}$ high speed 24 bit ADC channel. Each DAC is addressed via a single I2C bus by selecting a set of jumpers on the sampling head.

This invention is not limited to the Sensor Module described above. Many different types of sensors, sensor circuitry and sensor models may be used in this invention.

In some implementations of this invention, each sampler head includes a sensor lid that fits snugly over one or more IDA channels in the sampler head. In the example shown in FIGS. 11A and 11B, a sensor lid fits over as single IDA channel.

Figure 11A:
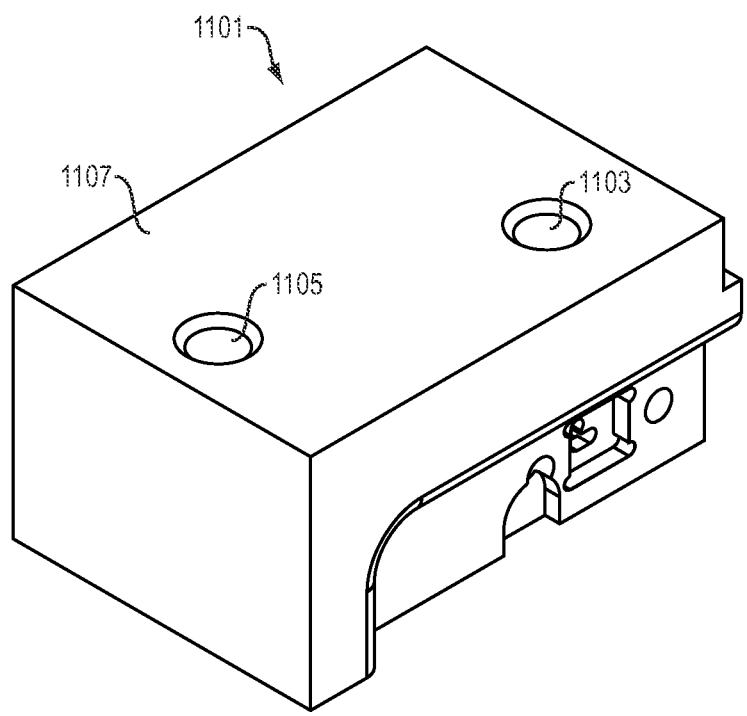
FIG. 11A is a perspective view of a sensor lid.

FIG. 11A is a perspective view of the exterior of a sensor lid 1101. Two holes 1103, 1105 at the top of sensor lid provide an inlet and outlet (or an outlet and inlet), respectively, for the sample being tested to flow into and out of the sampler.

Figure 11B:
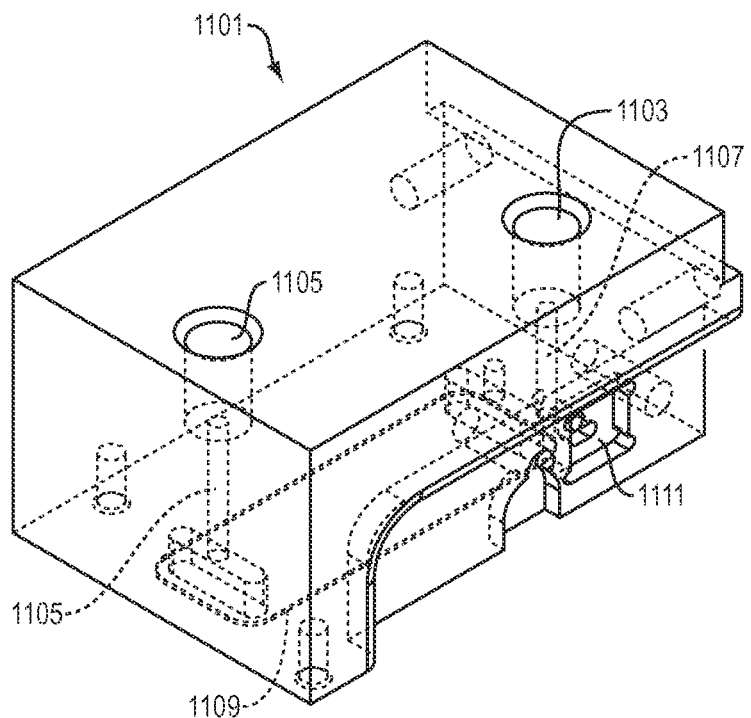
FIG. 11B shows some internal features of the same sensor lid.

FIG. 11B shows some internal features of the same sensor lid 1101. The bottom side of the bottom panel of the sensor lid can function as the top of a small perfusion chamber 1109. (In FIG. 11B, edges of the perfusion chamber 1109 look like an oval racetrack covering most of the length of the bottom of the lid.) The top of the perfusion chamber 1109 can be formed by the bottom of the sensor lid. The bottom of the perfusion chamber 1109 can be formed by an IDA, including the fingers and substrate of the IDA. The perfusion chamber 1109 may comprise a "ditch" in the IDA, tightly covered/sealed by the bottom of the sensor lid 1101. Tubing 1105, 1107 can connect the perfusion chamber 1109 to the inlet and outlet holes 1103, 1105, respectively. The tubing can be plastic or metal.

As a sample travels through the sensor lid 1101, the humidity and temperature of the sample are measured by a humidity/temperature sensor 1111 (a "T/RH sensor"). For example, depending on the direction a sample is traveling (i.e., from hole 1103 to hole 1105, or vice versa), the sample may flow through or past a T/RH sensor 1111 in the sensor lid immediately before or after the sample leaves the perfusion chamber 1109.

FET sensors can be highly sensitive to humidity. To first order any differential signal from FET sensors may be attributable to small changes in humidity. Even though room humidity stays constant, internal local humidities under each lid can vary. FET sensors can also be very sensitive to temperature. Local variations in temperature can cause differential sensor readings.

In illustrative embodiments of this invention, to avoid problems caused by local differences in temperature and relative humidity, a humidity/temperature sensor ("T/RH Sensor") 1111 can be used. The T/RH Sensor can provide local, real time, continuous humidity and temperature measurements of the sample stream that is being tested. The T/RH Sensor 1111 allows for fast debugging of perfusion problems. In addition, the signal may be calibrated to remove the part of the signal due to humidity and temperature variations. Such calibration may, for example, involve de-trending, deconvolving or adjusting a baseline. For example, such calibration may be performed if (i) a local difference in temperature or humidity is detected between two different channels in a sampler, or (ii) in order to standardize scent characterization across different machines.

In illustrative embodiments of this invention, the same gaseous sample that interacts with the channel also interacts, locally and in real time, with the T/RH sensor. The T/RH sensor is placed in the same stream as close as possible to the active area (e.g., perfusion chamber). The position and shape of T/RH sensor "nook" is such that part of the sample interacts with the T/RH sensor (i.e. no significant "cavitation" or local vortices or boundary layers occur for gas flows up to 1 L/min, which is well above what is actually necessary for sensing gases or liquids). The inlet and outlet and gasket placement of the T/RH sensor prevent dead volumes and the sample (e.g., gas) cannot bounce back through inlet for flows under 1 L/m; instead, the sample has to interact with T/RH sensor.

In the example shown in FIGS. 11A and 11B, the sensor lid 1101 comprises, at least in large part, a conducting material such as stainless steel. Thus, the sensor lid 1101 comprises a Faraday cage, which can protect the sensor against electromagnetic interference and static electricity accumulation and discharge. For example, the Faraday cage can reduce the electronics' and IDAs' susceptibility to RF and DC interference from (a) the sampler's own electronics, (b) neighboring boards, (c) external electrical devices, including cellular phones, and (d) static electricity hot spots that, being capable of pinpoint localization, could easily bump up the baseline of only one of the two channels creating the illusion of difference.

Interior and exterior surfaces of the sensor lid 1101 that come into contact with samples being tested can be made of polished, stainless steel. This tends to prevent adsorption of odorants to these surfaces facilitating fast returns to baseline by quick evacuations. Further, the sensor lid 1101 comprises a large (in this context) thermal mass, protecting the sensor against rapid changes in temperature.

Preferably, the volume of the perfusion chamber is very small, thereby allowing return to baseline to occur quickly. For example, the total volume of the perfusion chamber 1109 can be approximately 40 microliters.

FIGS. 12A and 12B illustrate (a) the importance of taking changes in relative humidity into account, and (b) two odor receptors responding differently to the same stimuli.

FIG. 12A is a chart of relative humidity vs. time, showing the response of an the T/RH sensor of a perfused chamber to ambient air and cyclohexanone. The vertical axis is percent relative humidity. The horizontal axis is time in seconds. Trace 1201 shows the response of the T/RH sensor to ambient air (during time periods 1203) and cyclohexanone (during time periods 1205).

FIG. 12B is a chart of unnormalized FET signal (current) vs. time data collected in the same sensor enclosure and at the same time as the RH % data collected by the T/RH sensor shown in FIG. 12A. In FIG. 12B, traces 1207 and 1209 show the response of two different odorant receptors to alternating samples of ambient air (during time periods 1203) and cyclohexanone (during time periods 1205). Trace 1207 is the response of RatOR 226. RatOR 226 is known to be non-specific to cyclohexanone, and because the ambient air and cyclohexanone sample have different relative humidities, the differential response of RatOR 226 to these alternating samples is due to changes in relative humidity. Trace 1209 shows the response of an odorant receptor commonly called Human OR17-210/OR1E3 ("OR17-210") to these same alternating samples. The left vertical axis is current in ×10 microamperes (for the RatOR 226 response); the right vertical axis is current in microamperes (for the OR17-210 response). The horizontal axis is time in seconds. The measurements for RatOR 226 were taken in Channel 3A (in one of the sampler heads in sampler 3); whereas the measurements for OR17-210 were taken in Channel 3B (in the other sampler head in sampler 3).

In FIG. 12B, the response of OR17-210 (Trace 1209) to the alternating samples of ambient air and cyclohexanone is counter to what would be predicted by relative humidity. This indicates that OR17-210's differential response to the alternating samples is due to OR17-210 being specific to cyclohexanone.

In exemplary implementations of this invention, one or more computer processors are specially adapted: (1) to control the operation of hardware components of the artificial olfactor, including electronic circuitry, electronic sensors, valves and pumps; (2) to perform computations for pattern recognition and scent matching; (3) to receive signals, including signals indicative of sensor readings or human input, (4) to output control signals, including control signals for controlling allosteric modulation of sensors and control signals for controlling transducers to output information in human perceivable format, and (5) to process data, perform computations, and control the read/write of data to and from memory devices. The one or more processors may be located in any position or positions within or outside of the artificial olfactor. For example: (1) at least some of the one or more processors may be embedded within or housed together with other components of the device, such as the samplers or their associated electronic boards or even collocated with the IDAs as surface mounted components, and (2) at least some of the one or more processors may be remote from other components of the device. The one or more processors may be connected to each other or to other hardware components in the artificial olfactor either: (1) wirelessly, (2) by wired connection, or (3) by a combination of wired and wireless connections. For example, items 461 and 527 in FIGS. 4 and 5 each, respectively, symbolize one or more of these computer processors.

Alternate Implementations:

This invention may be implemented in many ways, including ways other than those described above. Here are some non-limiting examples:

This invention is not limited to detecting odors in gaseous (or "dry") phase. For example, an artificial olfactor may be configured to operate in a liquid phase (loosely speaking, as an "E-tongue"). For liquid phase operation: (a) enclosures can be coated with non-conductive non-absorbent coating (e.g., polytetrafluoroethylene, Kapton® tape, or a non-porous insulating spray) to mitigate redox reactions; (b) electronic boards can be embedded into enclosures or made by surface-mounted electronic components collocated with the IDA on glass or on PCB boards; (c) rather than flow of a gas, a liquid may flow, using micro-fluidic technology; (d) odorant molecules may be dissolved or suspended in the liquid; and (e) if corrosive liquids are used, then any plastic tubing is preferably replaced by metal (although in many cases, liquid solvents would be mild and water based, so plastic tubing could be used). If GPCRs are used for liquid phase operation, then in illustrative implementations, the GPCRs would not be coated with the non-conductive, non-absorbent coating described above. However, as noted above, GPCRs may be covered with a hydrogel in order to stabilize them. Such a hydrogel may generally prevent the GPCRs from being in direct contact with a liquid test sample.

In liquid phase operation, a sample being tested may comprise, for example, water, blood, serum, urine, other aqueous solution, or other liquid solution or suspension.

All terms in the above descriptions of this invention that may imply a gaseous phase (e.g., "odorant", "odor", "scent", "smell", "olfactor", "olfaction", "air", "airborne", "volatile", "gas"or "perfuse") shall be construed as also extending to a liquid phase (e.g., by also implying a liquid phase, or by including or meaning their liquid phase analog). Also, the terms "substance", "compound" and "chemical" are not limited to any phase of matter. For example, a "substance" may be a gas, liquid or solid.

This invention is not limited to detecting scents that are perceptible to humans. For example, in some implementations, this invention may be used to detect an airborne compound (or combination of compounds) that seems odorless to a human, and that is present in any concentration in a sample of air.

In some implementations, this invention may achieve "sniffing" capabilities beyond what biological olfaction has evolved to do (e.g., to detect odorless volatiles such as the nerve gas Sarin or to operate in wet mode to detect any solute far beyond the mass range of biological noses or tongues).

This invention is not limited to an interdigitated micro-electrode array (IDA) with fingers made of platinum or gold.

Other conductors may be used for the IDA finger. Also, a 1-,2-, 3-, or 4-point probe can be used, instead of an IDA.

Depending on the particular implementation of this invention, sensor measurements may be taken in many different ways, including by potentiostatic, resistometric, galvanometric, cyclic chronoamerometric or cyclic voltametric measurements. Gating voltage, source-drain voltage or other bias voltages may be swept, and AC periods may be varied.

If a FET sensor is used, the FET may include a PPY nanotube (resulting in a highly sensitive gas sensor). For example, the PPY may comprise a co-polymer of pyrrole and pyrrole-3-carboxylic acid. Alternately, nanostructured semiconductors of high aspect ratio or nanocrystalline semiconductors of high surface to volume ratio can be used. For example, zinc-oxide (ZnO) nanowires, carbon nanotubes (CNT) or other semiconducting substrates can be used instead of PPYs. If ZnO nanowires are used: (a) the ZnO nanowires may be made solvothermally; (b) the odorant receptors may have a ZnO-binding sequence tag, and (c) short amino acid sequences can be included for oriented binding to the ZnO nanowires.

Protein expression pathways other than those described above can be used to create solubilized and stabilized GPCRs. For example, such alternate pathways include purification from mammalian cells, purification from $E.$ $coli$ cells, or cell-free expression systems. Also, for example: (1) the solubilization of GPCRs can be achieved by using surfactants/detergents (including peptide detergents); and (2) hydrogels may be used for stabilization of GPCRs.

Furthermore, proteins other than GPCR olfactory receptors (ORs) can be used to make the sensors selective. For example, one or more of the following may be used instead of GPCRs: ion channel coupled ORs, Vomeronasal Receptors, non-olfactory receptor GPCRs, odorant binding proteins (OBPs), synthetic receptors and other proteins (including (i) synthetic enzymes, and (ii) artificially soluble proteins, such as proteins made by replacing one or more hydrophobic amino acids in a transmembrane domain by one or more hydrophilic amino acids), synthetic or naturally occurring antibodies, aptamers, short pieces of DNA or RNA, specific peptide sequences or other antibodies or enzymes or polymers. More generally, any naturally occurring or synthesized "selectively sticky" material that reacts differentially to different molecules or features of molecules (or that reacts differently to given molecules or features of molecules under different conditions) may be employed instead of GPCRs.

In some implementations, this invention can match a target scent and test scent based on whether they include the same isotope of an element. Without being limited by theory, such isotope detection may utilize London dispersion forces, H-bonds or ligand residence times, or elastic and/or inelastic electron tunneling spectra each of which can depend on vibrational frequencies of odorant bonds and their interactions with the vibrational spectra of receptor subparts.

In some implementations, this invention may be calibrated for use as an analytical tool (e.g., to determine molecular ID and concentration of molecules in mixture similar to what a GC/MS would do).

In some implementations, this invention can operate as a "Yes/No" detector for specific compounds (e.g. TNT or 2,4 DNT as a signature of an explosive or methyl benzoate as the volatile handle for cocaine etc.) with very high sensitivity.

Figure 13:
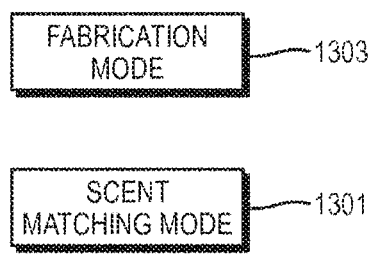
FIG. 13 shows fabrication and analysis modes.

This invention is not limited to operating in scent matching mode 1301. In some implementations, it may instead operate in fabrication mode 1303, as indicated by FIG. 13. When operated in fabrication mode, this invention can dynamically monitor the properties of layer-by-layer deposited films and adjusting deposition in real time, to meet given fabrication specifications. In some implementations, for example, this invention may be used in fabrication mode for: (i) nucleic acid nanoassembly, including DNA origami, and (ii) peptide and cluster programmable folding applications. Further, this invention may be used in fabrication mode for solid state synthesis or for synthesis in which assembly occurs without attachment to a solid substrate.

In a scent sensor, the number of IDA channels may vary (e.g., from one to four IDA channels). For example, a test channel flowing into a sensor may subdivide into multiple IDA channels, and then converge back into a single test channel that exits the sensor. Or, for example, multiple test channels flowing through IDAs may remain separate while entering, traversing and exiting a single sensor.

In some embodiments of this invention, one or more scent sensors are impedance sensors. Impedance sensors generally involve imposing a voltage at one or more frequency(ies) and measuring the resulting current. Exemplary sensors further include Field Effect Transistor (FET) sensors, which rely on the interaction of external charges with carriers in a semiconductor. FET sensors can offer enhanced sensitivity at low ionic strength.

In some implementations of this invention, one or more sensors provide baseline measurements. For example, one or more of the sensors providing baseline measurements may lack an odorant receptor.

In exemplary implementations, this invention includes data analysis hardware and software to identify through iterative, repeated or multiple measurements electrical inputs that provide indicative output signals in the presence of a selected contaminant, odorant, or target compound(s) in an olfactory background.

Each sensor may be self-contained and may have similar components internal to the sensor, such that electrical parameters that control the sensor may be available through input controls that are standardized among various sensors.

In some embodiments, this invention: (a) creates a table of classified substances without the need for an external correlation engine external to the system; or (b) uses arbitrarily long code words within an integrated detector and/or micro fluidic chamber without the need for an external sample handler.

In some implementations, a computer may (based on output of a prior sensor in a series of sensors) select a path or operating condition such that (1) a subsequent sensor in the series is tuned in order to operate within a dynamic range or to protect the subsequent sensor, or (2) a valve causes the sample which went through the prior sensor to travel to a subsequent sensor with a different semiconductor substrate (such as zinc oxide in the subsequent sensor, if PPY nanotubes were used in the prior sensor).

In some embodiments of this invention: (a) no prior training is needed; and (b) no attempt is made to identify a single odorant (or set of odorants that is unambiguously responsible for a scent. However, using such training or making such an attempt does not cause any embodiment to be outside the scope of this invention. For example, if it is known a priori that a positive scent control contains a signature odorant (e.g., vanillin) that is unambiguously responsible for a particular scent (e.g., the scent of vanilla), then total scent matching and allosteric modulation in accordance with principles of this invention would have the practical effect of identifying that specific odorant. Also, for example, even if prior training is not needed for total scent matching, adding prior training (e.g. with positive or negative control samples) may improve accuracy.

In some embodiments of this invention, a computer compares (a) all or part of a first scent pattern and (b) all or part of a second scent pattern, in order to determine whether two scents match. Thus, in some embodiments, this invention involves comparisons and matches of less than total scent patterns.

In some embodiments of this invention, one or more pressure sensors may be used to measure pressure in a sampler head locally and in real-time.

Definitions and Clarifications:

Here are a few definitions and clarifications. As used herein:

The terms "a" and "an", when modifying a noun, do not imply that only one of the noun exists.

The term "artificial olfactor" shall be construed broadly. For example, each of the following is an "artificial olfactor": (a) an apparatus configured to determine a match between a target scent and a test scent; (b) an apparatus configured to identify the scent of an airborne compound or combination of compounds; (c) an apparatus configured to detect the chemical identity of airborne compound; and (d) an apparatus configured to perform olfaction. For example, an artificial olfactor may include multiple scent sensors, T/RH sensors, processors and signal processing and signal acquisition circuitry. For example, an artificial olfactor may be used to match scent conferred by a volatile mixture in a gaseous environment, or by a solute in a liquid environment.

The phrases "allosteric modulation", "pair-wise allosteric modulation" and "n-wise allosteric modulation) are defined or clarified earlier in this document.

The phrase "between eleven and fifteen" means (a) in the case of real numbers, the closed interval [11, 15]; and (b) in the case of integers, 11, 12, 13, 14, 15. Similar expressions (e.g., expressions in the form of "between x and y") shall be construed in similar fashion.

The term "calibration" shall be construed broadly. For example, calibration may comprise any one or more of: (a) making any physical change to any apparatus, including any physical change to any sensor or to any signal processing hardware; (b) adjusting any circuit parameter or electrical parameter, including electrical inputs to sensors (including source-drain voltage, gating voltage and sweep rate) (c) adjusting any computation used to analyze or process data, including sensor data; (d) performing any kind of statistical normalization, (d) performing any kind of scaling, (e) applying any mathematical function, transformation or mapping to data, (f) detrending (e.g., detrending data so that effects of temperature and humidity are removed); (g) deconvolving; and (h) adjusting any baseline. For example, if the DI/I response of a first circuit to a stimuli is always twice the DI/I response of a second circuit to that stimuli, then scaling may be used to computationally calibrate the sensors, without making any physical change to the sensors, and such scaling would comprise a "calibration". If one or more computer processors use an algorithm to control allosteric modulation, and the algorithm uses calibrated data, then "allosteric modulation" (and computer control thereof) includes calibrating data (or taking into account calibration of data).

The term "compound" shall be construed broadly. Notwithstanding its common meaning, the term "compound" as used herein includes a pure chemical element, including a single atom or multiple atoms of a single element.

The term "comprise" (and grammatical variations thereof) shall be construed broadly, as if followed by "without limitation". If A comprises B, then A includes B and may include other things.

To say that a computer "declares" a match means that the computer determines a match. If one or more computer processors use a matching algorithm in order to determine a match, and the matching algorithm uses calibrated data, then "determining" the match includes calibrating data (or taking into account calibration of data). In order for a computer to "declare" (determine) a match, it is not necessary that the declaration or decision be expressed in a human-readable format (e.g., as text on a graphical user interface).

The terms "e.g." and "such as" mean for example.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each can be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes "a third" thing, a "fourth" thing and so on shall be construed in like manner.

A "group" means a set.

The terms "horizontal" and "vertical" shall be construed broadly. For example, "horizontal" and "vertical" may refer to two arbitrarily chosen coordinate axes in a Euclidian two dimensional space.

The term "include" (and grammatical variations thereof) shall be construed broadly, as if followed by "without limitation".

The term "loop" shall be construed broadly. For example, a curve that intersects itself is a "loop", regardless of its shape otherwise.

The term "odorant" means a chemical compound or element that creates, alone or in combination with other compounds, a scent. For example, an odorant may confer a scent that is detectable by a human, animal or machine. For example, the term "odorant" includes a volatile molecule that confers a scent. Also, for example, the term "odorant" includes a volatile molecule with an atomic mass of 600 Da or less. However, an "odorant" may have an atomic mass greater than 600 Da.

The term "or" is inclusive, not exclusive. For example "A or B" is true if A is true, or B is true, or both A or B are true. Also, for example, a calculation of "A or B" means a calculation of A, or a calculation of B, or a calculation of A and B.

A "pair" of things means two of the things.

A parenthesis is simply to make text easier to read, by indicating a grouping of words. A parenthesis does not mean that the parenthetical material is optional or can be ignored.

To say that two values a and b (where a≤b) differ by "x percent" (or by x %) means that x=(100(b−a))/b.

The term "perfuse" shall be construed broadly. For example, the term "perfuse" includes (a) dispersion of a volatile odorant into a gaseous sample, including a gaseous sample that is passed through a sampling enclosure, and (b) dispersion of a dissolved or suspended odorant into a liquid sample, including a liquid sample that is passed through a sampling enclosure.

In the context of determining whether a scent that is being tested matches a target scent: (a) the target scent is a "positive control", (b) a "negative control" is a scent that is known to be different than the target scent, and (c) a "null control" is a test sample to which neither a positive control nor a negative control has been added. Consider an example in which an artificial olfactor is being used to track an escaped criminal. In this example: (a) an item known to have been recently worn by the criminal would confer a scent that is a positive control; (b) an item known to have recently been worn by the jail warden and never touched by the criminal would confer a scent that is a "negative control"; and (c) ambient air brought into the artificial olfactor to which neither a positive control nor a negative control has been added is a "null control." As used herein, a "null control sample" is sometimes called a test sample and the scent of a "null control sample" is sometimes called a test scent.

A "set" consists of one or more items. Notwithstanding common usage, the term "set" as used herein does not include a null set (i.e., a set with no elements). A first set and a second set may be disjoint, overlapping or identical. For example, a first set of sensors and a second set of sensors may have no sensors in common or some but not all sensors in common. Also, for example, a first set of sensors and a second set of sensors may be identical sets consisting of the exact same sensors (and thus actually be the same single set).

The term "scent" shall be construed broadly. For example, the term "scent" includes any one or more of the following: (a) an overall olfactory experience of a sample; (b) stimuli (e.g., a volatile compound or combination of volatile compounds) that give rise when smelled (or would give rise, if smelled) to this overall olfactory experience; and (c) a volatile compound or combination of volatile compounds that is odorless to a human.

The terms "in series" and "in parallel" shall be construed broadly. An example of an "in series" arrangement is: a set of scent sensors arranged such that a sample flows through a first sensor in the set, then through a second sensor in the set, and so on. An example of an "in parallel" arrangement is: a set of scent sensors arranged such that a sample divides and part of the sample flows through each of the sensors in the set respectively, without first flowing through any other sensors in the set (disregarding any repeated loops through this setup as a whole).

Two values a and b are "significantly different" if they differ by more than 10%.

Two values a and b are "substantially" the same or "substantially" identical if they differ by 50% or less. For example, two DC voltages are substantially identical if they differ by 50% or less. Or, for example, two AC voltages are substantially identical if their RMS voltages differ by 10% or less. Two values a and b are "substantially" different if they differ by 50% or less.

The term "sweep" shall be construed broadly. For example, a "sweep" of an electrical parameter (e.g., a DC voltage or an AC peak-to-peak voltage) may comprise: (i) starting at the minimum value of the parameter during the sweep and then increasing to the maximum value of the parameter during the sweep, or vice versa; (ii) starting at the minimum value of the parameter during the sweep, then increasing to the maximum value of the parameter during the sweep, then decreasing to the minimal value of the parameter (or vice versa), or (iii) starting at a starting value of the electrical parameter, then changing the parameter to one of the extrema (i.e., maximum or minimum) for the sweep, then changing the parameter to the other extrema (e.g., maximum or minimum) for the sweep, then changing the parameter back to the starting value. The electrical parameter may vary continuously or discretely during a sweep. The term "sweep" includes measuring output from the sensor while the electrical parameter varies.

The term "Tsweep" is defined or clarified earlier in this document.

The terms "Vsd" and "Vg" are defined or clarified earlier in this document.

Unless the context clearly requires otherwise, any description of any computation by a computer (including any determination by a computer) shall be construed as a high-level description. For example, a single step of a high-level description may actually involve many steps of machine-level behavior in the computer, such as many steps of machine-code level computations, or many physical changes in logic voltage.

A list of multiple steps in a method (or process) does not imply, except to the extent that the context requires otherwise, that: (1) the steps occur in any particular order or sequence, including the order or sequence listed; (2) the steps occur only once; (3) the different steps occur the same number of times during the process, or (4) a particular step is applied to the same thing each time that the particular step occurs.

Grammatical variations of defined terms shall be construed in like manner as the defined terms. For example, if a verb is defined in one conjugation, then other conjugations of that verb shall be construed in like manner. Or, for example, if a noun is defined in one declension, then other declensions of that noun shall be construed in like manner. Or for example, the phrase "significantly differ" shall be construed in like manner as "significantly different." Or, for example, the adjective "calibrated" shall be construed in like manner as the defined noun "calibration".

More Variations:

This invention may be implemented in many different ways. Here are more non-limiting examples.

This invention may be implemented as a method of determining whether or not a test scent conferred by a test sample matches a target scent conferred by a target sample, which method comprises, in combination: (a) using a portion of a test sample as a null control sample, (b) creating a positive control sample by adding all or part of the target sample to another portion of the test sample; (c) measuring a positive control response and a null control response, the positive control response comprising response of a first set of sensors to the positive control sample, and the null control response comprising response of a second set of sensors to the null control sample; and (d) using one or more processors to determine whether or not the target scent matches the test scent; wherein, if the one or more processors make a determination that the target and test scent match, the one or more processors make this determination only after: (i) the positive control response and the null control response are each measured under multiple different test conditions during allosteric modulation of one or more sensors, out of the first or second sets of sensors; and (ii) the one or more processors determine that the positive control response does not match the null control response under any of the multiple different test conditions. Furthermore: (1) the allosteric modulation may comprise pair-wise allosteric modulation of one or more pairs of sensors, which pairs each respectively include a sensor in the first set of sensors and a sensor in the second set of sensors; (2) the target sample and test sample may each be in liquid phase; (3) the first and second sets of sensors may each be calibrated to respond orthogonally or semi-orthogonally to the positive control sample; (4) the first and second sets of sensors may each may be arranged in series; (5) the method may further comprise moving the positive control sample in a loop more than one time through the first set of sensors, or moving the null control sample in a loop more than one time through the second set of sensors; (6) (i) a sample may pass through a subsequent sensor after passing through a prior sensor, (ii) the method may further comprise using at least one processor to output control signals to make an adjustment to the subsequent sensor, before the sample reaches the subsequent sensor, which adjustment is based at least in part on output from the prior sensor, and (iii) the prior and subsequent sensors may each be sensors in the first set of sensors, or may each be sensors in the second set of sensors; and (7) the adjustment may comprise an adjustment to an electric field applied to a region in which odorant molecules in the sample interact with the subsequent sensor.

This invention may be implemented as a method of determining whether or not a test scent conferred by a test sample matches a target scent conveyed by a target sample, the method comprising, in combination: (a) using a portion of a test sample as a null control sample, (b) creating a positive control sample by adding all or part of the target sample to another portion of the test sample; (c) creating a negative control sample by adding all or part of a negative sample to another portion of the test sample; (d) measuring a positive control response, a negative control response and a null control response, the positive control response comprising response of a first set of sensors to the positive control sample, the negative positive control response comprising response of a second set of sensors to the negative control sample, and the null control response comprising response of a third set of sensors to the null control sample; and (e) using one or more processors to determine whether or not the target scent matches the test scent; wherein, if the one or more processors make a determination that the target and test scent match, the one or more processors make this determination only after (i) a computer determines that the test scent matches scent of the negative control, or (ii) both (A) the positive control response and the null control response are each measured under multiple different test conditions, which multiple different test conditions occur during allosteric modulation of one or more sensors out of the first, second or third sets of sensors, and (B) the one or more processors determine that the positive control response does not match the null control response under any of the multiple different test conditions. Furthermore, (1) the first, second and third sets of sensors may each be calibrated to respond orthogonally or semi-orthogonally to the positive control sample; (2) (i) the first and second sets of sensors may each be arranged in series, (ii) a sample may pass through a subsequent sensor after passing through a prior sensor, (iii) the method may further comprise using at least one processor to output control signals to make an adjustment to the subsequent sensor, before the sample reaches the subsequent sensor, which adjustment is based at least in part on output from the prior sensor, (iv) the adjustment may comprise an adjustment to an electric field applied to a region in which odorant molecules in the sample interact with the subsequent sensor; and (v) the prior and subsequent sensors may each be sensors in the first set of sensors, or may each be sensors in the second set of sensors, or may each be sensors in the third set of sensors; and (3) the allosteric modulation may comprise n-wise allosteric modulation of one or more groups of sensors, which groups of sensors each respectively include a sensor in the first set of sensors, a sensor in the second set of sensors, and a sensor in the third set of sensors.

This invention may be implemented as a method comprising, in combination: (a) measuring test responses, the test responses comprising responses of a first set of sensors to a test sample under multiple testing conditions during allosteric modulation of one or more sensors in the first set of sensors; (b) using one or more processors to compare (i) the test responses and (ii) recorded responses of a second set of sensors to one or more positive controls under the multiple testing conditions; and (c) using one or more processors to determine whether or not scent conferred by the test sample matches scent conferred by all or some of the one or more positive controls. Furthermore: (1) the first, second and third sets of sensors may each be calibrated to respond orthogonally or semi-orthogonally to the positive control sample; (2) (i) the first and second sets of sensors may each be arranged in series, (ii) a sample may pass through a subsequent sensor after passing through a prior sensor, (iii) the method may further comprise using at least one processor to output control signals to make an adjustment to the subsequent sensor, before the sample reaches the subsequent sensor, which adjustment is based at least in part on output from the prior sensor, (iv) the adjustment may comprise an adjustment to an electric field applied to a region in which odorant molecules in the sample interact with the subsequent sensor; and (v) the prior and subsequent sensors may each be sensors in the first set of sensors, or may each be sensors in the second set of sensors; (3) the method may further comprise moving the test sample in a loop more than one time through the first set of sensors; and (4) the method may further comprise temporarily immobilizing all or part of the test sample in a sensor undergoing the variation.

This invention may be implemented as apparatus comprising, in combination: (a) n sets of scent sensors, wherein each of the sets of scent sensors (i) are calibrated (or are adapted to be calibrated) to respond orthogonally or semi-orthogonally to a positive control scent and (ii) are arranged in series; (b) one or more valves for controlling whether a sample flowing through a specific set of scent sensors, out of the n sets of scent sensors, flows more than one time through the specific set of sensors; and (c) one or more processors for (i) outputting control signals to n-wise allosterically modulate one or more groups of scent sensors, each of the one or more groups including at least one scent sensor from each of the n sets of scent sensors; and (ii) determining whether or not a scent conferred by a test sample matches a scent conferred by the positive control sample. Furthermore: (1) (i) a particular set of scent sensors, out of the n sets of scent sensors may include a prior scent sensor and a subsequent scent sensor, and may be configured such that a sample flowing through the particular set of scent sensors passes through the subsequent scent sensor after passing through the prior scent sensor, and (ii) the one or more processors may be adapted to output control signals to make an adjustment to the subsequent sensor, before the sample reaches the subsequent sensor, which adjustment is based at least in part on output from the prior sensor and comprises an adjustment to an electric field applied to a region in which odorant molecules in the sample interact with the subsequent sensor; and (2) the apparatus may further comprise a plurality of relative humidity sensors positioned such that each respective relative humidity sensor, out of the plurality of relative humidity sensors, is positioned adjacent to a respective scent sensor, out of scent sensors comprising the n sets of scent sensors.

CONCLUSION

While exemplary implementations are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention. Numerous modifications may be made by one of ordinary skill in the art without departing from the scope of the invention.

What is claimed is:

1. Apparatus for determining whether or not a test scent conferred by a test sample matches a target scent conveyed by a target sample, which apparatus comprises, in combination:
   (a) a first set of scent sensors configured for measuring a null control response, which null control response comprises response of the first set of sensors to a null control sample, which null control sample comprises a portion of the test sample; and
   (b) a second set of scent sensors configured for measuring a positive control response, which positive control response comprises response of the second set of sensors to a positive control sample, which positive control sample comprises another portion of the test sample and all or part of the target sample;
   (c) a third set of scent sensors configured for measuring a negative control response, which negative control response comprises response of the third set of sensors to a negative control sample, which negative control sample does not contain any of the target sample; and
   (d) one or more processors configured for determining whether or not the target scent matches the test scent, such that if the one or more processors make a determination that the target and test scent match, the one or more processors make this determination only after:
      (i) the positive control response, negative control response, and the null control response are each measured under multiple different test conditions, which multiple different test conditions occur during allosteric modulation of one or more sensors out of the first, second or third sets of sensors, and
      (ii) the one or more processors determine that (A) the positive control response matches the null control response under all of the multiple different test conditions, and (B) the negative control response matches the null control response under none of the multiple different test conditions.

2. The apparatus of claim 1, wherein the allosteric modulation comprises n-wise allosteric modulation of one or more groups of sensors, which groups of sensors each respectively include a sensor in the first set of sensors, a sensor in the second set of sensors, and a sensor in the third set of sensors.

3. The apparatus of claim 1, wherein the target sample and test sample are each in liquid phase.

4. The apparatus of claim 1, wherein the first, second and third sets of sensors are each calibrated to respond orthogonally or semi-orthogonally to the positive control sample.

5. The apparatus of claim 1, wherein the apparatus includes valves for directing movement of the positive control sample in a loop more than one time through the second set of sensors.

6. The apparatus of claim 1, wherein the first and second sets of sensors are each arranged in series.

7. The apparatus of claim 6, wherein:
   (a) a particular set of scent sensors, out of the first and second sets of scent sensors (i) includes a prior scent sensor and a subsequent scent sensor, and (ii) is configured such that a sample flowing through the particular set of scent sensors passes through the subsequent scent sensor after passing through the prior scent sensor;
   (b) the one or more processors are configured to output control signals to make an adjustment to the subsequent sensor, before the sample reaches the subsequent sensor, which adjustment is based at least in part on output from the prior sensor.

8. The apparatus of claim 7, wherein the adjustment comprises an adjustment to an electric field applied to a region in which odorant molecules in the sample interact with the subsequent sensor.

9. The apparatus of claim 1, wherein the apparatus includes valves for temporarily immobilizing all or part of a sample in a sensor undergoing the allosteric modulation.

10. The apparatus of claim 1, further comprising a plurality of relative humidity sensors positioned such that each respective relative humidity sensor is positioned adjacent to a scent sensor.

* * * * *